(12) United States Patent
Frederick

(10) Patent No.: US 12,171,682 B2
(45) Date of Patent: Dec. 24, 2024

(54) THUMB BRACE

(71) Applicant: Hugh Allen Frederick, Dallas, TX (US)

(72) Inventor: Hugh Allen Frederick, Dallas, TX (US)

( * ) Notice: Subject to any disclaimer, the term of this patent is extended or adjusted under 35 U.S.C. 154(b) by 1029 days.

(21) Appl. No.: 16/921,042

(22) Filed: Jul. 6, 2020

(65) Prior Publication Data

US 2021/0007873 A1   Jan. 14, 2021

Related U.S. Application Data

(60) Provisional application No. 62/871,281, filed on Jul. 8, 2019.

(51) Int. Cl.
*A61F 5/01* (2006.01)
*A41D 19/00* (2006.01)
(Continued)

(52) U.S. Cl.
CPC ........ *A61F 5/0118* (2013.01); *A41D 19/0048* (2013.01); *A41D 19/01523* (2013.01);
(Continued)

(58) Field of Classification Search
CPC .... A61F 5/0118; A61F 5/013; A61F 5/05866; A61F 13/10; A61F 13/104; A61F 13/105; A61F 13/107; A41D 19/0048; A41D 19/01523; A41D 19/01582; A41D 19/01588; A41D 2300/32; A41D 2400/32;
(Continued)

(56) References Cited

U.S. PATENT DOCUMENTS 1,315,035 A   9/1919  Post
3,707,730 A   1/1973  Slider
(Continued)

FOREIGN PATENT DOCUMENTS

JP   H07255894 A   10/1995
JP   2006083480 A   3/2006
(Continued)

OTHER PUBLICATIONS

Translation of KR-200403073-Y1 (Year: 2005).*
(Continued)

*Primary Examiner* — Keri J Nelson
*Assistant Examiner* — Seth R. Brown
(74) *Attorney, Agent, or Firm* — Conley Rose, P.C.; Rodney B. Carroll

(57) ABSTRACT

A thumb brace comprising a glove having a thumb portion disposed between a palm side and a back side and comprising a first attachment region positioned adjacent a base of the thumb portion and a second attachment region positioned on the back side of the glove; a first elastic strap whereby the first strap extends a distal end of a thumb metacarpal bone of a user of the brace; a second elastic strap having a first end attached to the palm side of the glove and the second end releasably attached to the second attachment region, whereby the second strap reduces a proximal end of a thumb metacarpal bone of a user of the brace; and a pad attached to the glove such that the pad cushions a CMC joint of the user of the brace from impact.

20 Claims, 18 Drawing Sheets

(51) Int. Cl.
*A41D 19/015* (2006.01)
*A63B 71/14* (2006.01)
*A63B 102/32* (2015.01)

(52) U.S. Cl.
CPC ...... *A41D 19/01582* (2013.01); *A63B 71/146* (2013.01); *A41D 2300/32* (2013.01); *A41D 2400/32* (2013.01); *A41D 2500/50* (2013.01); *A63B 2102/32* (2015.10); *A63B 2209/00* (2013.01); *A63B 2209/10* (2013.01)

(58) Field of Classification Search
CPC ........ A41D 2500/50; A41D 13/08–088; A63B 71/141; A63B 71/146; A63B 2071/0694; A63B 2102/32; A63B 2209/00; A63B 2209/10; A63B 2225/09
See application file for complete search history.

(56) References Cited

U.S. PATENT DOCUMENTS

| | | |
|---|---|---|
| 4,057,255 A | 11/1977 | Bishop |
| 4,561,122 A | 12/1985 | Stanley et al. |
| 4,643,428 A | 2/1987 | Churchill |
| 4,658,441 A | 4/1987 | Smith |
| 4,658,445 A | 4/1987 | Tribble |
| 4,730,354 A | 3/1988 | Saito |
| 5,004,231 A | 4/1991 | Alread |
| 5,018,221 A | 5/1991 | Romandetto |
| 5,414,868 A * | 5/1995 | Crawford ............. A63B 71/146 2/160 |
| 5,787,896 A | 8/1998 | Sackett |
| 5,899,890 A | 5/1999 | Deirmendjian et al. |
| 6,261,252 B1 * | 7/2001 | Darcey ............... A61F 5/05866 602/5 |
| 6,783,507 B1 | 8/2004 | Fisher |
| 7,056,298 B1 * | 6/2006 | Weber .................. A61F 5/0118 2/21 |
| 7,770,723 B2 | 8/2010 | Hajduk |
| 7,882,571 B2 | 2/2011 | Robba et al. |
| 8,425,339 B2 | 4/2013 | Basden |
| 9,504,282 B1 * | 11/2016 | Frederick ......... A41D 19/01582 |
| 10,349,692 B2 | 7/2019 | Frederick |
| 2004/0060096 A1 | 4/2004 | Thiruppathi |
| 2004/0216216 A1 | 11/2004 | Terris et al. |
| 2005/0028244 A1 | 2/2005 | Roeckl |
| 2005/0268374 A1 | 12/2005 | Mattesky |
| 2007/0174948 A1 | 8/2007 | Robba et al. |
| 2009/0260129 A1 | 10/2009 | Elkowitz |
| 2011/0138513 A1 | 6/2011 | Giddins |
| 2012/0179081 A1 | 7/2012 | Anglada et al. |
| 2015/0157483 A1 | 6/2015 | Grunden et al. |
| 2016/0022501 A1 * | 1/2016 | Schultz ............. A61F 13/00038 602/43 |
| 2017/0215497 A1 * | 8/2017 | Frederick .............. A61F 5/0118 |
| 2018/0132553 A1 * | 5/2018 | Quirk ............... A41D 19/01588 |
| 2019/0281907 A1 | 9/2019 | Frederick |

FOREIGN PATENT DOCUMENTS

| | | | |
|---|---|---|---|
| KR | 200403073 Y1 * | 12/2005 | ............. A63B 71/14 |
| KR | 20120122391 A | 11/2012 | |
| WO | 2017132090 A1 | 8/2017 | |
| WO | WO-2018136748 A1 * | 7/2018 | ......... A61F 5/05866 |

OTHER PUBLICATIONS

Filing receipt and specification for provisional patent application entitled "Thumb Saver Glove," by Hugh Allen Frederick, filed Jan. 28, 2016 as U.S. Appl. No. 62/288,112.
Filing receipt and specification for provisional patent application entitled "Thumb Brace," by Hugh Allen Frederick, filed Jul. 8, 2019 as U.S. Appl. No. 62/871,281.
Foreign communication from a related application—International Preliminary Report on Patentability, Application No. PCT/US2017/014550, dated Aug. 9, 2018, 14 pages.
Foreign communication from a related application—International Search Report and Written Opinion of the International Searching Authority of International Application No. PCT/US2017/014550, dated Apr. 18, 2017, 19 pages.
Office Action dated Sep. 28, 2024 U.S. Appl. No. 18/093,697, filed Jan. 5, 2024.

* cited by examiner

THUMB BRACE

CROSS-REFERENCE TO RELATED APPLICATIONS

The present application claims benefit of U.S. Provisional Patent Application No. 62/871,281 filed Jul. 8, 2019, by Dr. Hugh Allen Frederick, and entitled "Thumb Brace," which is incorporated herein by reference in its entirety for all purposes.

BACKGROUND

The joint where the thumb connects to the wrist may be referred to as the carpometacarpal joint, the CMC joint, or the basal joint of the thumb. Arthritis affecting the CMC joint affects millions of people and may be caused by genetic inherited factors and/or wear and tear on the joint with repeated use over many years. Thumb CMC arthritis may cause pain during gripping and pinching actions and may limit hand function. Such symptoms may begin when patients are in their fifties and still active.

There is no cure for arthritis. Current treatments for thumb CMC arthritis include suggesting that patients modify their activity by doing less with their hands, suggesting that patients take arthritis medication, applying splints or braces to the affected area, injecting cortisone into the affected area, and performing surgery on the affected area.

SUMMARY

In an embodiment, a thumb brace is provided. The thumb brace comprises: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove, whereby the first strap extends a distal end of a thumb metacarpal bone of a user of the brace; a second elastic strap having a first end, a mid-portion, and a second end, wherein the first end is attached to the palm side of the glove and the second end is releasably attached to the second attachment region, whereby the second strap reduces a proximal end of a thumb metacarpal bone of a user of the brace; and a pad attached to the glove and positioned proximate the second attachment region and adjacent the base of the thumb portion on the back side of the glove such that the pad cushions a CMC joint of the user of the brace from impact In another embodiment, a thumb brace is provided. The thumb brace comprises: a glove comprising first, second, and third hook and loop fasteners, wherein the first hook and loop fastener provides an adjustable cuff opening for the glove; the second hook and loop fastener connects first and second ends of a first elastic strap positioned on the glove to extend a distal end of a thumb metacarpal bone of a user of the glove; the third hook and loop fastener connects the second end of a second elastic strap positioned on the glove to reduce a proximal end of a thumb metacarpal bone of a user of the glove; and a pad attached to the glove and positioned proximate the base of the thumb such that the pad cushions a CMC joint of the user of the brace from impact.

In another embodiment, a method for aligning a thumb metacarpal bone with a trapezium bone via a thumb brace comprising a glove, a pad, and a strap system, the method comprising: placing the glove on a hand experiencing subluxation of the thumb metacarpal bone; extending a distal end of the thumb metacarpal bone by releasably connecting a first elastic strap of the strapping system to a first attachment region on the glove; and reducing a proximal end of the thumb metacarpal bone by releasably connecting a second elastic strap to a second attachment region of the glove, and the method further comprising cushioning a CMC joint of the user of the brace from impact via the pad.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Figure 1:
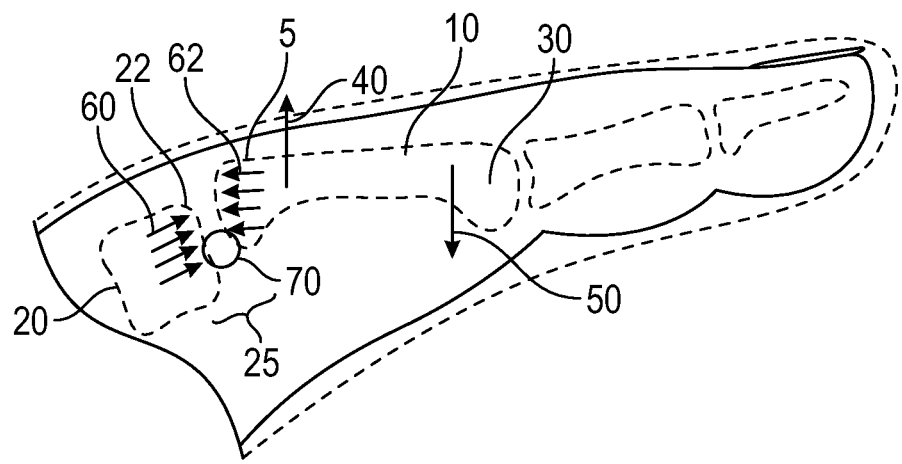
FIG. 1 illustrates dorsal subluxation of the proximal end of the thumb metacarpal bone in a patient with arthritis in the thumb metacarpal bone.

FIG. 1 illustrates dorsal subluxation (as represented by arrow 40) of the proximal end 5 of the thumb metacarpal bone 10 in a patient with arthritis in the carpometacarpal (CMC) joint 25. During routine pinching and grasping activities, significant forces may be applied across the CMC joint 25 in an area of the joint about the size of a nickel. When arthritis is not present, these forces may be spread evenly over the ends of the thumb metacarpal bone 10 and the trapezium bone 20 at the interface where those two bones meet. With repeated use, the shear stress on the CMC joint 25 may cause wear on the cartilage caps on the proximal end 5 of the thumb metacarpal bone 10 and the distal end 22 of the trapezium bone 20. Subsequent inflammation may stretch the capsule and ligaments around the CMC joint 25. As a result, the proximal end 5 of the thumb metacarpal bone 10 may sublux dorsally (as represented by arrow 40) away from the trapezium bone 20, and the distal end 30 of the thumb metacarpal bone 10 may move in the opposite direction (as represented by arrow 50), toward the palm. This orientation of the thumb metacarpal causes all of the forces that were previously spread evenly over the ends of the thumb metacarpal bone 10 and the trapezium bone 20 to become concentrated in only the small portion of the CMC joint 25 where the thumb metacarpal and the trapezium now meet. More specifically, with the thumb metacarpal bone 10 in a dorsal subluxation, it can be seen that the forces between the thumb metacarpal bone 10 and the trapezium bone 20, indicated by opposing reference arrows 60 and 62, are concentrated in a small area 70 rather than being distributed evenly across the entire interface between the thumb metacarpal bone 10 and the trapezium bone 20 as would be the case if the thumb metacarpal bone 10 and the trapezium bone 20 were properly aligned. With only a portion of the CMC joint 25 surface absorbing the repeated load, the cartilage may fail and arthritis and pain may develop.

A thumb splint may stabilize or immobilize the thumb and reduce the pain experienced by a patient with such a condition. However, a patient may not be able to satisfactorily engage in sports or other vigorous activities while wearing a thumb splint since the splint may impede use of the hand. Gloves designed for use by arthritic patients while playing golf or engaging in other activities merely provide padding around the joints and do not stabilize the thumb.

Referring to the Figures and the related disclosure herein, various embodiments of a thumb brace 200 are provided that stabilize and align the thumb metacarpal bone 10 without impeding the wearer's ability to engage in sports or other activities. The thumb brace 200 comprises a glove 100 and a strap system 105 that includes a first strap 110 designed to lift or extend the distal end 30 of the thumb metacarpal bone 10 and a second strap 150 designed to reduce the dorsal subluxation at the proximal end 5 of the thumb metacarpal bone 10 at the CMC joint 25. These two forces (e.g., counter-rotating forces applied proximate and opposite reference arrows 40 and 50) provided by straps 110 and 150 align and stabilize the CMC joint 25 such that the load is distributed across the entire joint interface, thereby reducing pain and abnormal wear on the CMC joint 25.

Figure 3:
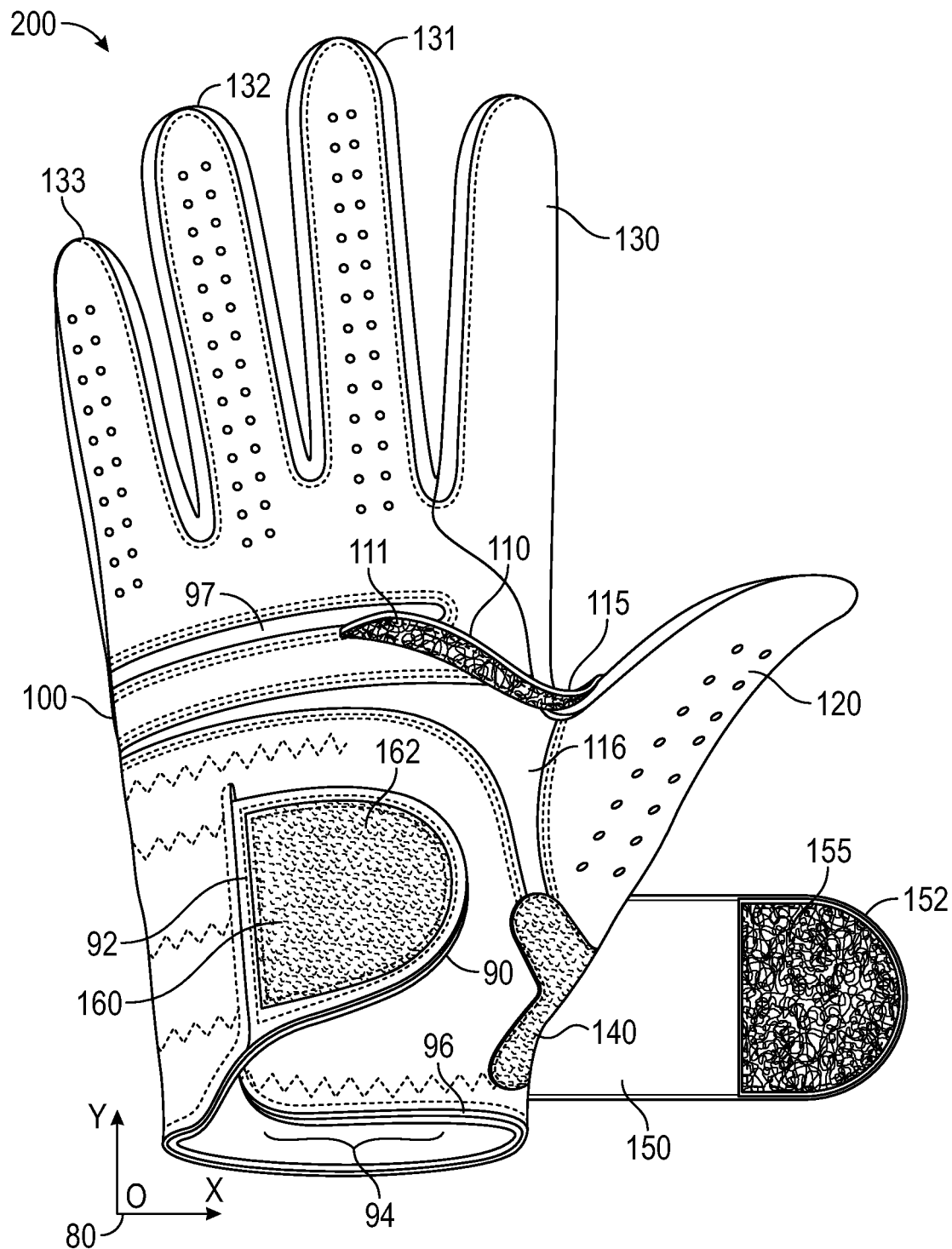
FIG. 3 is a back view of a thumb brace according to an embodiment of the present disclosure.

As used herein, the term "glove" may refer to any article in which a hand may be inserted and that at least partially contacts and at least partially covers the back of the hand and the palm of the hand. Referring to FIG. 3, the glove may also include finger elements, e.g., 130, 131, 132, 133, into which fingers can be inserted. A finger element may be present for each of the four fingers, or one or more finger elements may be absent to allow one or more fingers to be free to perform activities that may be hindered by the presence of a finger element. Additionally or alternatively, each finger element may be a full element enclosing the entire length and tip of a given finger, or may be a partial or shortened finger element where a portion of the finger is covered and the remaining portion extending to the tip is uncovered. That is, when a finger element is present, the finger element may cover the entire finger, or the finger element may cover only a portion of the finger and the rest of the finger may be exposed. In an embodiment, the glove comprise 4 finger elements, alternatively 3 finger elements, alternatively 2 finger elements, alternatively 1 finger element, or alternatively no finger elements; and each finger element that is present may independently be a full or partial finger element. The glove disclosed herein includes a thumb element into which a thumb can be inserted. The thumb element may cover the entire thumb or only a lower portion of the thumb, for example terminating at the joint between proximal and distal phalanges of the thumb.

The strap system 105 disclosed herein can be incorporated into any suitable glove for any suitable purpose to provide therapeutic support to a person having thumb CMC arthritis and wearing the glove during a given activity. Examples of suitable gloves for use with the currently described thumb brace 200 include those designed or configured for activities such as construction, where users work with hardware such as hammers, saws, nail guns, building materials, and the like; oil and gas exploration and production, where users such as roughnecks work with heavy equipment on onshore and offshore drilling rigs; motorsports and transportation service and repair, where mechanics work with tools, impact wrenches, jacks, and the like; logging, where users work with chainsaws and axes; tactical operations performed by military and law enforcement personnel; cutting activities performed by butchers, commercial fisherman, or meat processing workers; outdoor activities, where users grip a variety of specialized equipment while participating in activities such as golf, tennis, baseball, softball, dirt biking, snowmobiling, skiing, snowboarding, hunting, fishing, hiking, climbing, cycling, rollerblading, skateboarding, water skiing, wake boarding, and the like; lawn and gardening, where users work with a variety of hand tools such as hoes, shovels, rakes, mowers, trimmers, and the like; and home improvement, where weekend warriors undertake a myriad of home improvement activities. Further examples of suitable gloves for use with the currently described thumb brace 200 include one or more of the various types of Mechanix Wear® gloves, commercially available from Mechanix Wear, Inc. Further examples of suitable gloves for use with the currently described thumb brace 200 include one or more of the various golf, batting, or other sporting gloves commercially available from FootJoy, Nike, Callaway, Titleist, Taylor Made, Dunlop, Bionic, Puma, Pocketec, Mizuno, Bridgestone, Under Armour, Franklin, Easton, and others.

In an embodiment, the glove 100 comprises a partial thumb element terminating at the joint between proximal and distal phalanges of the thumb and 4 partial finger elements terminating at about (e.g., adjacent or proximate to) the joint between the proximal and middle phalange of each finger, for example of the type commonly referred to as a workout or weight lifting glove. In an embodiment, the glove 100 comprises three full finger elements covering the middle, ring, and pinky fingers, and a partial finger element for the index finger, for example of the type commonly referred to as a shooting glove allowing easy access of the index finger to a trigger of a firearm. In an embodiment, the glove 100 has 4 full finger elements and a full thumb element and is not substantially thicker than existing golf gloves, batting gloves, or the like and therefore does not impede the wearer's ability to engage in sports or other activities such as golf, tennis, baseball or softball. In an embodiment, the glove 100 is of a type commonly referred to and configured as a batting glove for use in baseball or softball.

In an embodiment, the glove 100 is of a type commonly referred to and configured as a golf glove, and for ease of reference the remainder of the description herein will be in the context of a golf glove embodiment with the understanding that the concepts and designs herein (e.g., the strap system 105 as described herein) may be incorporated into any suitable glove for any suitable purpose. Golf gloves typically have a natural or synthetic leather palm and a variety of fabric backs, often incorporating one or more cooling elements such as vents (e.g., perforations); flexible mesh portions (e.g., across the knuckles); stretchable, moisture-wicking, and/or breathable fabric; and combinations thereof. The palm and/or palm side of one or more of the finger elements may further incorporate a number of texturing options to improve grip. Referring to FIG. 3, a golf glove may have an adjustable cuff, for example an elastic cuff or an adjustably sized cuff as provided by a tab closure such as flap 90 on the back of the glove (i.e., dorsal or back side of the hand) that may be opened or closed by way of a fastener such as a hook and loop fasteners, zipper, etc. The flap 90 has an external face or surface 92 that is typically a smooth fabric (often adorned by a manufacturer's logo) in a standard golf glove (but, in contrast, embodiments according to the present disclosure may further comprise second attachment region 160 on external flap surface 92, as will be described in detail herein). The flap 90 typically further comprises an interior face or surface comprising a first portion (e.g., loop portion) of the hook and loop fastener. The flap 90 overlaps a portion 94 of the back of the glove having disposed thereon the opposite portion of the hook and loop fastener (e.g., the hook portion) such that the glove flap 90 may be adjustably closed and opened by engaging and disengaging, respectively, the hook and loop fastener portions associated with the flap 90 and overlapped portion 94 of the back of the glove.

Referring to FIG. 3, in addition to glove 100, the thumb brace 200 comprises a strap system 105, which may be combined or incorporated with any suitable glove as described herein. The strap system 105 further comprises a first strap 110, a second strap 150, a first attachment region 140, and a second attachment region 160. As used herein, the term "strap" may refer to any article that is substantially longer than wide, for example a rectangular shape of various dimensions. In some embodiments disclosed herein, the strap may be made of a stretchable, elastic material to allow the strap to be stretched such that the ends of the strap may be placed in various desired locations on the attachment regions. Examples of suitable stretchable, elastic material include elastomeric fabrics, for example fabrics comprising fibers made from natural or synthetic elastomeric materials such as natural or synthetic rubber, spandex or elastane, lastol, and elasterell-p. As described in more detail below and shown in FIG. 2, first strap 110 may be a single, continuous piece of material having a first end 111 and a second end 112. Alternatively, first strap 110 may be two separate pieces of material (also referred to as first and second lengths, members, sections, or halves of the first strap), each of which having an end that performs a function similar to that performed by a corresponding end 111 or 112 of a single piece of material. In an embodiment, the first strap 110 may have a total combined, unstretched length of about 4, 4.5, 5, 5.5, 6, 6.5, 7, 7.5, 8, 8.5, 9, 9.5, 10, 10.5, 11, 11.5, or 12 inches, and a width of about 0.25, 0.3, 0.4, 0.5, 0.6, 0.7, 0.75, 0.8, 0.9, 1.0, 1.1, 1.2, or 1.25 inches. Excess length may be trimmed by a user to provide a customized fitting. In an embodiment, the first strap 110 has a length in a range of from about 7 to 9 inches and a width in a range of from about 0.25 to 0.75 inches.

Figure 4:
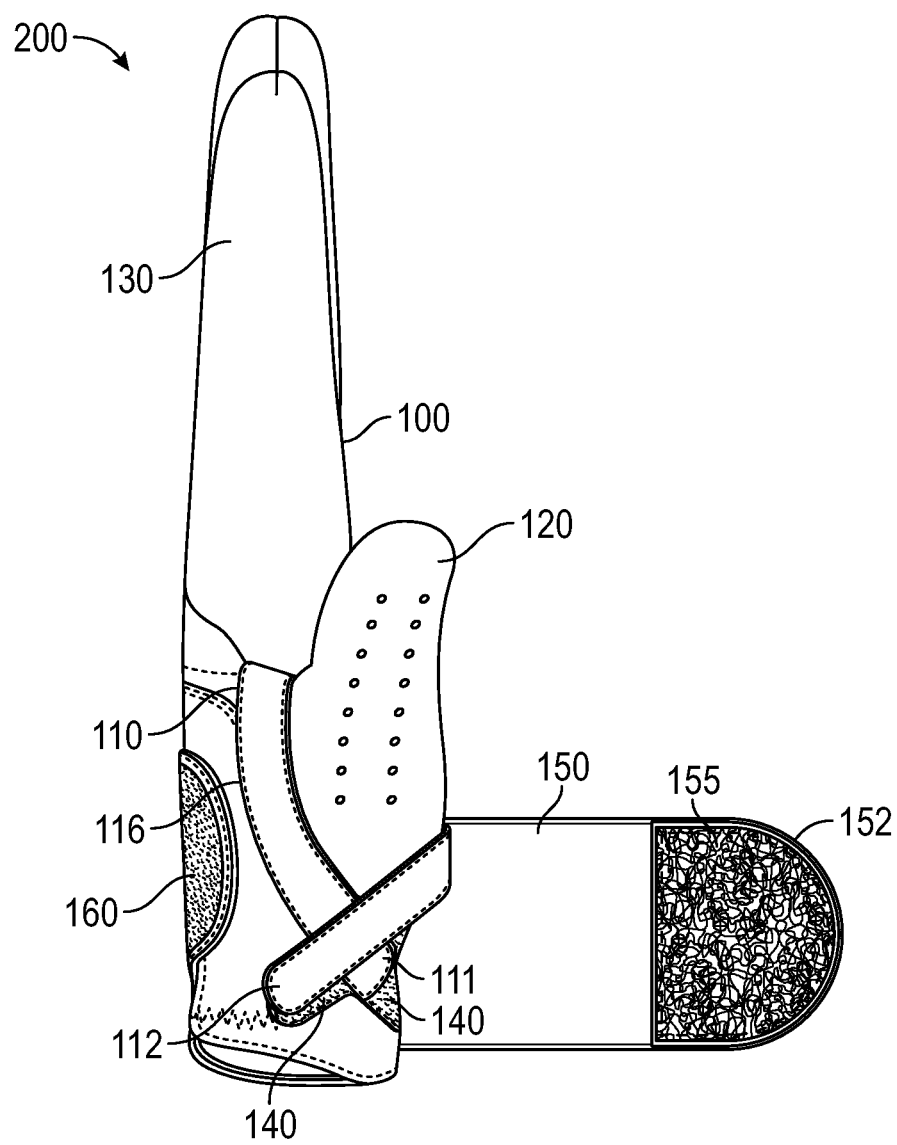
FIG. 4 is a side view of a thumb brace according to an embodiment of the present disclosure.
Figure 7:
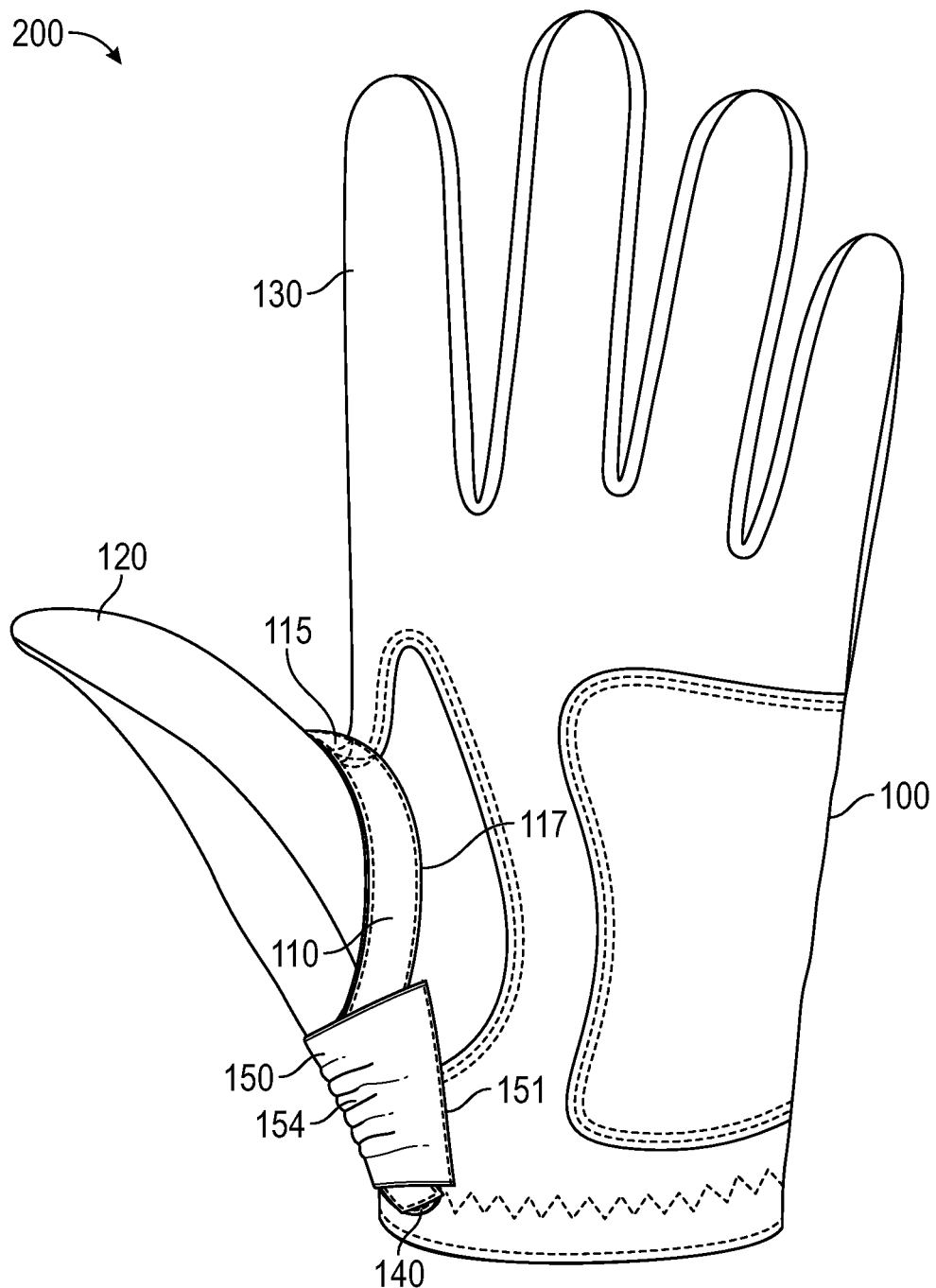
FIG. 7 is a palm view of a thumb brace according to an embodiment of the present disclosure.

Referring to FIG. 3, a central portion 115 of the first strap 110 is disposed in a region of the glove 100 where a thumb element 120 of the glove 100 merges with a first finger element 130 of the glove 100. Several embodiments for disposing the first strap 110 within this region of the glove (e.g., cradle 118) will be discussed below with reference to FIGS. 8, 9, and 10. As shown in FIG. 4, first end 111 of the first strap 110 remote from the central portion 115 may be stretched, placed over and in contact with a dorsal region 116 of the glove 100 adjacent the base of the thumb of the glove, further wrapped around and in contact with the base of the thumb, and attached to the glove 100 via first attachment region 140. The second end 112 of the first strap 110 remote from the central portion 115 may be stretched, placed over and in contract with a palmar region 117 (as shown in FIG. 7) of the glove 100 adjacent the thumb of the glove, further wrapped around and in contact with the base of the thumb, placed over and in contact with the first end 111 adjacent the termination thereof, and attached to the glove 100 via an unused or open portion of the first attachment region 140. Alternatively, the ends 111 and 112 of the first strap 110 may be attached to the first attachment region 140 in the reverse order.

The first attachment region 140 provides a complementary mating or attachment surface for the ends 111 and 112 of first strap 110 such that the ends 111 and 112 will be held securely in place upon contact with first attachment region 140. As such ends 111 and 112 and first attachment region 140 may comprise a complementary portion of a fastener such as a hook and loop fabric attachment system such as Velcro® brand hook and loop fastener. In the embodiments shown in the Figures, the attachment of ends 111 and 112 of first strap 110 to the first attachment region 140 of glove 100 occurs through the use of a hook and loop fabric fastener. In other embodiments, other attachment means or fasteners, such as snaps or buttons, may be used. It should be understood that when attachment by a hook and loop fastener is described herein, one of the two surfaces being attached includes the hook fabric portion of the fastener and the other surface includes the loop fabric portion, and typically the hook and loop fabric portions may be placed on either surface opposite each other (that is, the hook and loop fabric portions of the fastener are typically reversible in position or sequence).

Figure 2:
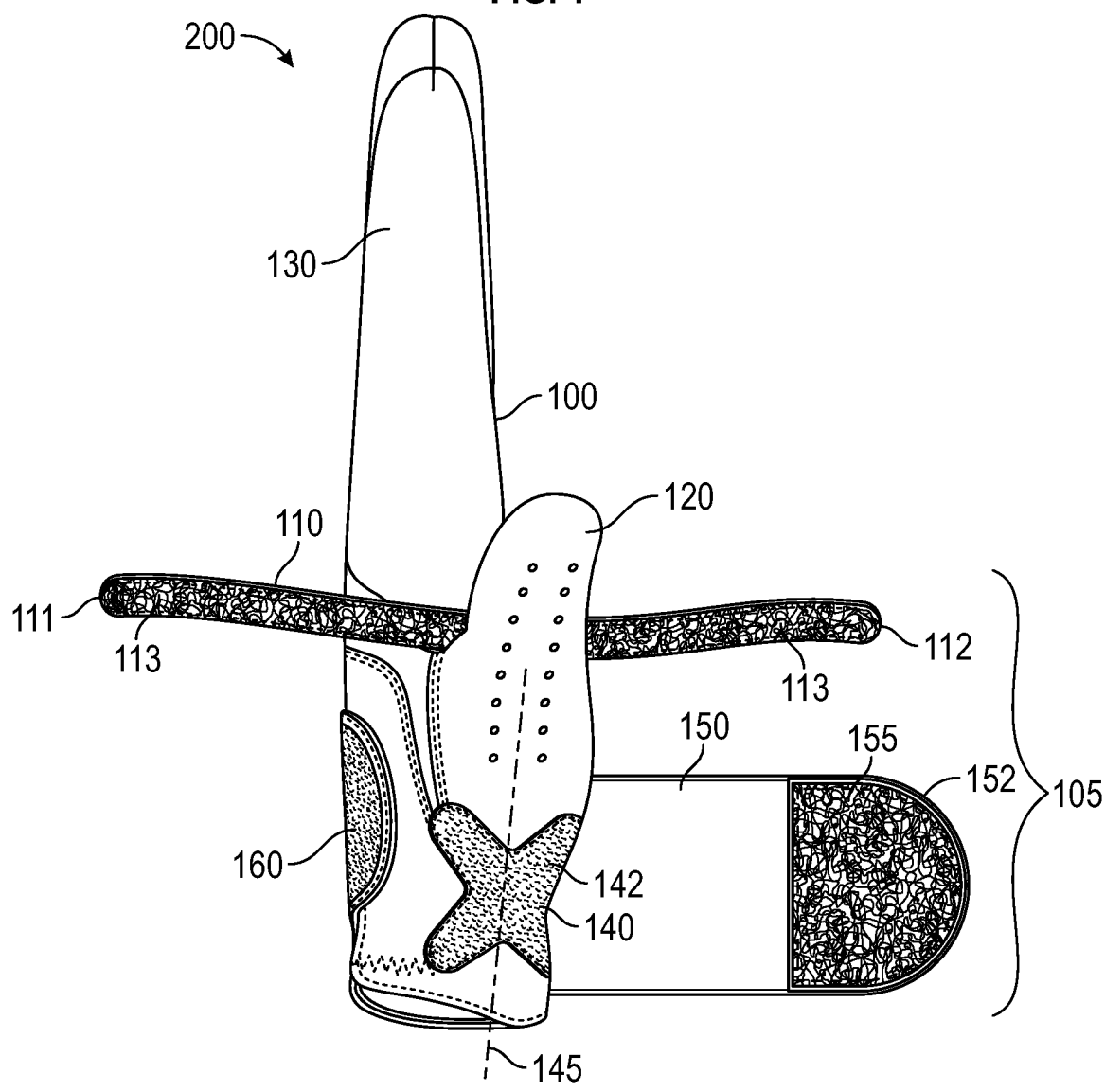
FIG. 2 is a side view of a thumb brace according to an embodiment of the present disclosure.

In an embodiment shown in FIGS. 2 and 3, at least a portion of the underside 113 of the first strap 110 adjacent the ends 111 and 112 comprises the loop fabric portion of the hook and loop fastener, that is, the underside 113 of ends 111 and 112 of the first strap 110 that attach to and detach from the first attachment region 140 of glove 100. At least a portion of the exterior surface 142 of the first attachment region 140 of the glove 100 comprises the hook fabric portion of the hook and loop fastener. The hook and loop fabric portions of the fastener may be attached to the glove 100 and first strap 110, respectively, by any suitable attachment means such as stitching and/or adhesive.

Figure 13:
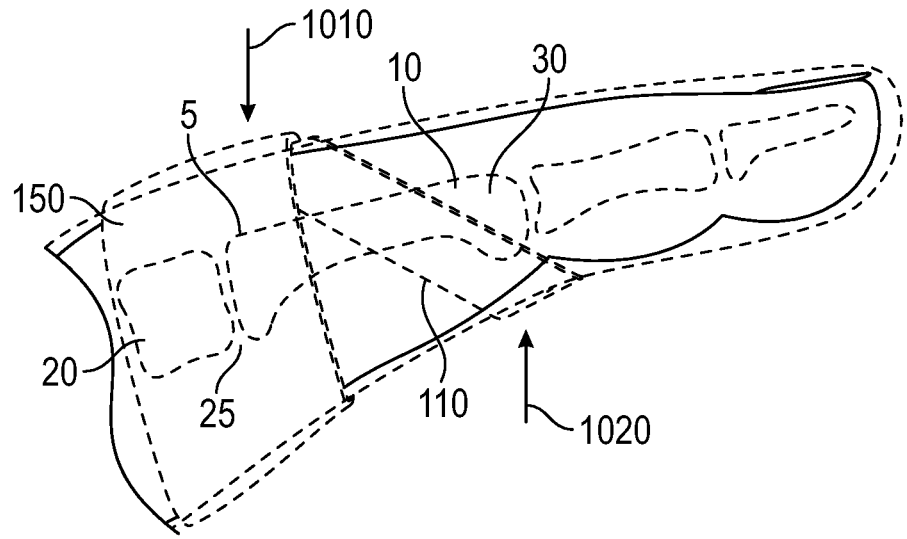
FIG. 13 is a side view of a thumb brace illustrating the attachment of a strapping system to the thumb brace according to an embodiment of the present disclosure.

The first attachment region 140 of glove 100 (e.g., comprising the hook fabric portion of the fastener) may be positioned such that upon stretching and attaching ends 111 and 112 of first strap 110 as described herein, a force counter to the direction of subluxation of metacarpal bone 10 is applied to the distal end 30 of metacarpal bone 10 as shown by reference arrow 1020 in FIG. 13. In an embodiment, the first attachment region 140 of glove 100 (e.g., comprising the hook fabric portion of the fastener) may be disposed on the dorsal side of the hand adjacent the base of the thumb, for example between the base of the thumb and the wrist, or alternatively at or adjacent where the thumb and wrist meet (e.g., at or adjacent the intersection of the trapezium 20 and the scaphoid bone). In an embodiment, the first attachment region 140 of glove 100 (e.g., comprising the hook fabric portion of the fastener) may be disposed on the dorsal side of the hand adjacent the base of the thumb, for example between the base of the thumb and the wrist, or alternatively at or adjacent where the thumb and wrist meet (e.g., at or adjacent the intersection of the trapezium 20 and the scaphoid bone), wherein about equal surface area is symmetrically disposed on either side of axis 145 running along a surface ridge of the thumb (e.g., positioned adjacent a base of the thumb, or thumb portion of the glove, along a midline defined by axis 145 where the palm side of the glove and the back side of the glove meet). In an embodiment, the first attachment region 140 of glove 100 (e.g., comprising the hook fabric portion of the fastener) may be disposed on the radial side of the wrist and dorsal to the thumb CMC joint 25. In an embodiment, the first attachment region 140 of glove 100 (e.g., comprising the hook fabric portion of the fastener) may be disposed on the radial side of the wrist between the CMC joint 25 and the intersection of the trapezium 20 and the scaphoid bone.

The first attachment region 140 may be of any suitable size and shape. In an embodiment, the first attachment region 140 may have a surface area in a range of between about 0.25 in$^2$ and about 5 in$^2$; alternatively, between about 0.25 in$^2$ and about 4 in$^2$; alternatively, between about 0.5 in$^2$ and about 4 in$^2$; alternatively, between about 0.75 in$^2$ and about 3 in$^2$; alternatively, between about 1 in$^2$ and about 3 in$^2$; alternatively, between about 1 in$^2$ and about 2.5 in$^2$; alternatively, between about 1.5 in$^2$ and about 3.5 in$^2$; alternatively, between about 1.5 in$^2$ and about 3.0 in$^2$; alternatively, between about 2.0 in$^2$ and about 4 in$^2$; or alternatively, between about 2.0 in$^2$ and about 3.5 in$^2$.

In an embodiment, the first attachment region 140 may include one or more indicators to indicate preferred positions at which the ends 111 and 112 of the first strap 110 should be attached to the first attachment region 140. For example, as shown in FIGS. 2, 3, 4, and 11, the first attachment region 140 has the shape of an "X" or a cross, where each leg of the "X" indicates a preferred alignment of one of the ends 111 or 112 of the first strap 110. In other embodiments, the first attachment region 140 may have another shape, such as an oval, circle, star, square, or rectangle. In such cases, preferred alignments of the ends 111 and 112 of the first strap 110 may be indicated by lines, coloring, contrasting, or other indicators superimposed or otherwise visible on the first attachment region 140. For example, an indicator forming an "X" shape substantially similar to that shown in FIG. 2, or any other indicator providing a preferred alignment position for ends 111 and 112 of first strap 110, may be printed or otherwise shown, for example via contrasting hook and loop fastener fabric color forming the alignment pattern.

When a person dons the glove 100, each end 111 and 112 of the first strap 110 may be passed over one side or the other of the wearer's thumb and attached to the first attachment region 140 via the hook and loop fastener, and the ends 111 and 112 may be attached in any order. The first attachment region 140 may be of such a size that, after the first end 111 (having a loop portion of the fastener) of the first strap 110 is attached, a sufficient amount of hook fastener remains exposed such that the second end 112 of the first strap 110 (having a loop portion of the fastener) may be positioned over the first end 111 and attached to the glove by means of the remaining exposed portion of hook fastener in the first attachment region 140. In an embodiment, a topside surface of first strap 110 opposite the underside 113 and adjacent the first end 111 may comprise a portion of hook fastener such that after the first end 111 is attached to the glove, the second end 112 of first strap 110 may be positioned over the first end 111 and attached to the glove by both the topside surface of first strap 110 adjacent the first end 111 and by means of the remaining exposed portion of hook fastener in the first attachment region 140. As described herein, the first strap 110 may be made of an elastic material that allows the ends 111 and 112 of the first strap 110 to be stretched to a desired position on the first attachment region 140.

When the ends 111 and 112 of the first strap 110 are tautly stretched and attached to the first attachment region 140 in such a manner as described herein, the first strap 110 lifts or extends the distal portion 30 of the thumb metacarpal bone 10, for example as shown by reference arrow 1020 in FIG. 13.

Referring to FIGS. 2 and 3, the strap system 105 further comprises a second strap 150. The second strap 150 may be made of an elastic material that allows the second strap 150 to be stretched to a desired position on the second attachment region 160. In an embodiment, the second strap 150 may have a total combined, unstretched length of about 4, 4.0, 5, 5.5, 6, 6.5, 7, 7.5, 8, 8.5, 9, 9.5, 10, 10.5, 11, 11.5, or 12 inches, and a width of about 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, or 2.0 inches. Excess length may be trimmed by a user to provide a customized fitting. In an embodiment, the second strap 150 has a length in a range of from about 4 to 6 inches and a width in a range of from about 0.75 to 1.25 inches.

As shown in FIG. 7, a first end 151 of the second strap 150 may be attached to the glove 100 near the palm side of the wrist portion of the glove 100. In an embodiment, the first end 151 of the second strap 150 may be attached to the glove 100 near the palm side of the wrist portion of the glove 100 along an axis 153 extending substantially parallel with a mid-line of the index finger element of the glove. In alternative embodiments, the first end 151 of the second strap 150 may be positioned substantially parallel with and from about 0.1, 0.2, 0.25, 0.3, 0.4, 0.5, 0.6, 0.7, 0.75, 0.8, 0.9, or 1.0 inches on either side of axis 153. In alternative embodiments, the first end 151 of the second strap may be positioned at an angle with respect to axis 153 and having opposing ends terminating at a location from about 0.1, 0.2, 0.25, 0.3, 0.4, 0.5, 0.6, 0.7, 0.75, 0.8, 0.9, or 1.0 inches on either side of axis 153. The first end 151 of the second strap 150 may be fixedly attached to the glove 100 by stitching, adhesive (e.g., glue), or other known attachment means. Alternatively, the first end 151 of the second strap 150 may be removably attached to the glove 100, for example via hook and loop fastener, wherein the underside 155 of second strap 150 comprises loop fabric and contacts an area of hook fabric disposed on (e.g., stitched and/or adhered) the palm of the glove proximate the locations described in this paragraph. Removably attaching the second strap 150 to the glove 100 by hook and loop fastener allows the user to adjust the length of the second end 152 of the second strap 150 by varying the placement thereof, or otherwise adjust the positioning, comfort, or support provided by the thumb brace 200. In an embodiment, rather than the second strap 150 being a separate component that is attached to the glove 100, the glove 100 may be manufactured such that first end 151 of the second strap 150 is an integral component of the glove 100 near the palm side of the wrist portion of the glove 100.

Figure 5:
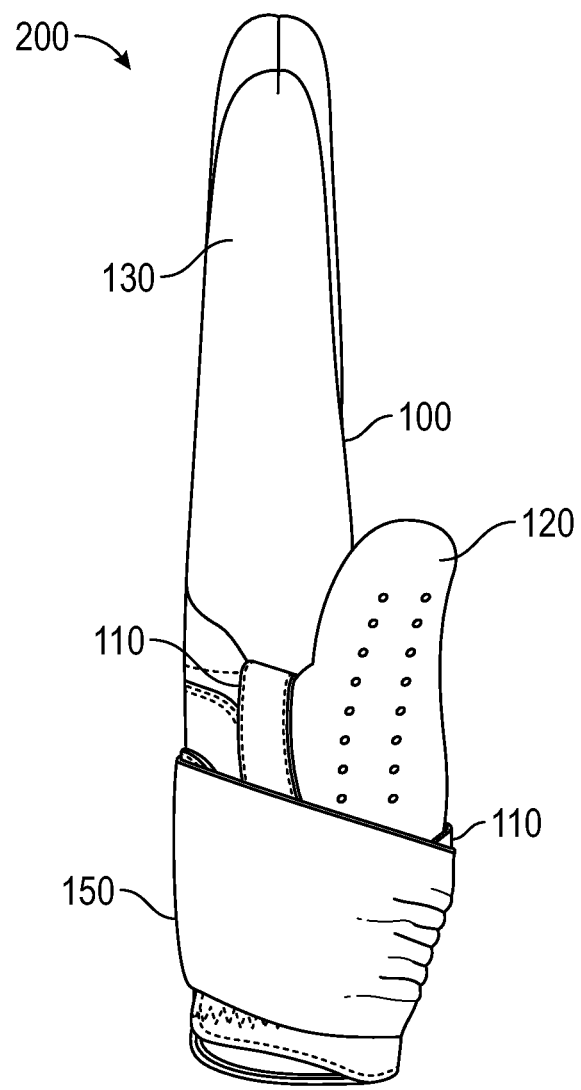
FIG. 5 is a side view of a thumb brace according to an embodiment of the present disclosure.
Figure 6:
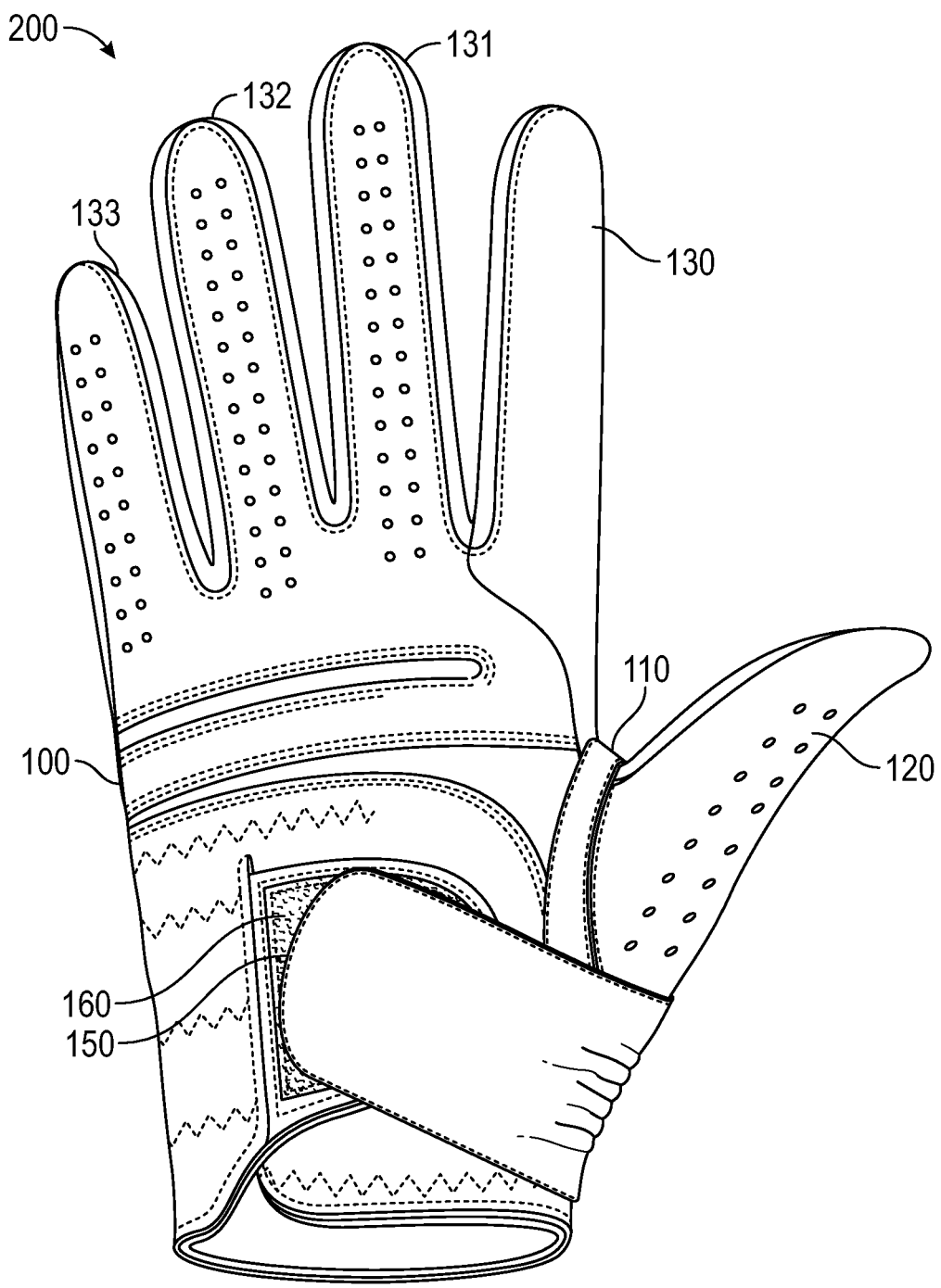
FIG. 6 is a back view of a thumb brace according to an embodiment of the present disclosure.
Figure 11:
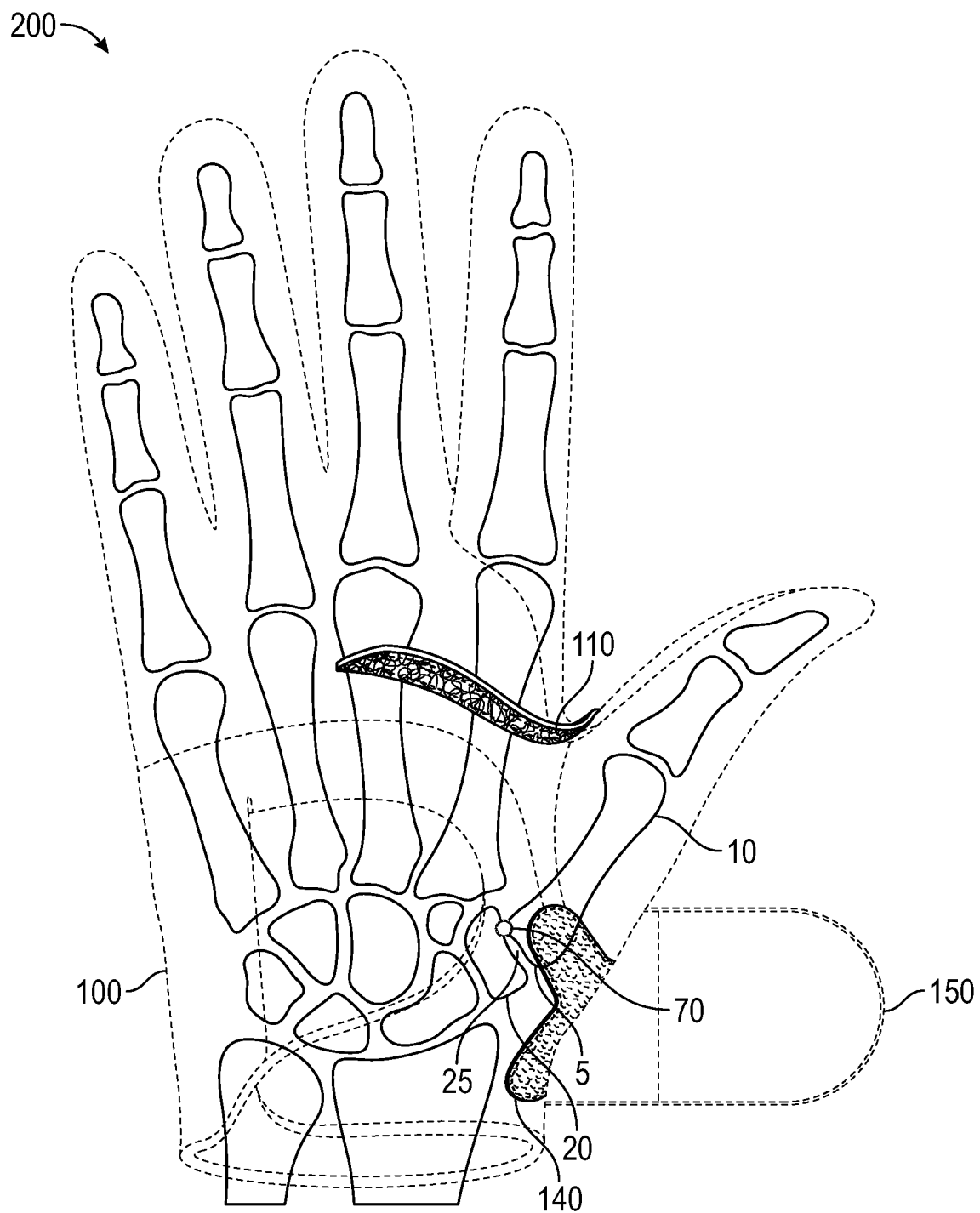
FIG. 11 illustrates an outline of a thumb brace superimposed over a dorsal view of the bones of a left human hand according to an embodiment of the present disclosure.

After the ends 111 and 112 of the first strap 110 have been attached to the first attachment region 140 as described above, the second, loose end 152 of the second strap 150 may be stretched, wrapped around and in contact with an area 154 adjacent the base of the thumb of the glove (as shown in FIG. 7), passed over and substantially covering and in contact with ends 111 and 112 attached to the first attachment region 140, and attached to a second attachment region 160 on the back (i.e., dorsal) side of the wrist portion of the glove 100. FIG. 5 illustrates a side view, FIG. 6 illustrates a back or dorsal view, and FIG. 7 illustrates a palm side view of the glove 100 after the ends 111 and 112 of first strap 110 and the second end 152 of the second strap 150 have been attached to the first attachment region 140 and the second attachment region 160, respectively, of the glove 100 as described above. In passing over the CMC joint 25 in this manner (as shown in FIGS. 6 and 11), the second strap 150 may pass over the ends 111 and 112 of the first strap 110, thereby further securing the ends 111 and 112 of the first strap 110 to the first attachment region 140. Stretching the second strap 150 taut and attaching the second end 152 of the second strap 150 to the second attachment region 160 of the glove 100 in such a manner provides a force vector palmarly at the dorsal CMC joint 25 to help reduce dorsal subluxation of the thumb metacarpal bone 10, for example as represented by reference arrow 1010 in FIG. 13. With the first strap 110 extending the distal portion 30 of the thumb metacarpal bone 10 (as represented by reference arrow 1020) and the second strap 150 reducing dorsal subluxation of the thumb metacarpal bone 10 (as represented by reference arrow 1010), the alignment of the CMC joint 25 is improved. The entire joint thus shares in any load on the joint, and pain and abnormal wear on the joint are reduced.

The second attachment region 160 provides a complementary mating or attachment surface for the second end 152 of second strap 150 such that second end 152 will be held securely in place upon contact with second attachment region 160. As such second end 152 and second attachment region 160 may comprise a complementary portion of a fastener such as a hook and loop fabric attachment system such as Velcro® brand hook and loop fastener. In the embodiments shown in the Figures, the attachment of second end 152 of second strap 150 to the second attachment region 160 of glove 100 occurs through the use of a hook and loop fabric fastener. Alternatively, attachment of the second strap 150 to the back side of the wrist portion of the glove 100 may occur via snaps, buttons or other attachment means.

In an embodiment shown in FIGS. 2, 3, and 4, at least a portion of the underside 155 of the second strap 150 adjacent the second end 152 comprises the loop fabric portion of the hook and loop fastener, that is the side of the second strap 150 that attaches to and detaches from the second attachment region 160 of glove 100. At least a portion of the exterior surface 162 of the second attachment region 160 of the glove 100 comprises the hook portion of the hook and loop fastener such that the second strap 150 may attach to the back side of the wrist portion of the glove 100 by means of the hook and loop fastener. The hook and loop fabric portions of the fastener may be attached to the glove 100 and second strap 150, respectively, by any suitable attachment means such as stitching and/or adhesive.

The second attachment region 160 of glove 100 (e.g., comprising the hook fabric portion of the fastener) may be positioned such that upon stretching and attaching second end 152 of second strap 150 as described herein, a force counter to the direction of subluxation of metacarpal bone 10 is applied to the proximal end 5 of metacarpal bone 10 as shown by reference arrow 1010 in FIG. 13. The second attachment region 160 may be located on the back or dorsal side of the glove 100, for example in an area located near the midsection of the back of the glove. With reference to an x-y axis 80 having an origin at the leftmost edge of the wrist of the glove 100 as shown in FIG. 3, the second attachment region 160 may be located anywhere substantially within a region defined as from about 0.5 to about 3 inches from the origin along the x axis and from about 0.5 to about 3.5 inches from the origin along the y axis; alternatively, within a region defined as from about 1.0 to about 2.5 inches from the origin along the x axis and from about 0.5 to about 3.5 inches from the origin along the y axis; alternatively, within a region defined as from about 1.0 to about 2.5 inches from the origin along the x axis and from about 1.0 to about 3.0 inches from the origin along the y axis; or alternatively, within a region defined as from about 1.0 to about 2.5 inches from the origin along the x axis and from about 1.0 to about 2.5 inches from the origin along the y axis. As shown in FIG. 3, in an embodiment, second attachment region 160 may be located on the back side of the glove between the edge or cuff 96 of the glove 100 and a knuckle portion 97 of the glove 100.

As shown in FIG. 3, many golf gloves and other gloves of the type described herein include a strap, tab or flap 90 that may be used to loosen or tighten the glove around the wearer's wrist. In an embodiment, the back side of flap 90, that is, the external flap surface 92 facing away from the glove 100, may be the second attachment region 160 which includes a hook fabric portion of the fastener and to which the second end 152 of the second strap 150 (having a loop fabric portion) may be attached. In an embodiment, the second attachment region 160 comprises a patch of hook fabric having a corresponding size and shape about equal to the flap 90 and stitched onto the external flap surface 92 of flap 90, as is shown in FIG. 3. In other embodiments, the second attachment region 160 may have any suitable shape, such as an oval, circle, star, square, or rectangle. If a glove does not include such a flap 90, a portion of the fastener (e.g., a hook portion of fabric) to provide the second attachment region 160 may be placed on any portion of the back side of the glove that allows the second strap 150 to be positioned to provide the desired reduction in dorsal subluxation of the thumb metacarpal bone 10.

The second attachment region 160 may be of any suitable size and shape. In an embodiment, the second attachment region 160 may have a surface area in a range of between about 0.25 $in^2$ and about 5 $in^2$; alternatively, between about 0.25 $in^2$ and about 4 $in^2$; alternatively, between about 0.5 $in^2$ and about 4 $in^2$; alternatively, between about 0.75 $in^2$ and about 3 $in^2$; alternatively, between about 1 $in^2$ and about 3 $in^2$; alternatively, between about 1 $in^2$ and about 2.5 $in^2$; alternatively, between about 1.5 $in^2$ and about 3.5 $in^2$; alternatively, between about 1.5 $in^2$ and about 3.0 $in^2$; alternatively, between about 2.0 $in^2$ and about 4 $in^2$; or alternatively, between about 2.0 in² and about 3.5 in². In an embodiment, the second attachment region 160 may include one or more indicators to indicate preferred positions at which the second end 152 of the second strap 150 should be attached to the second attachment region 160.

The strap system 105 may be operatively positioned in relationship to, and optionally coupled with, the glove 100 to provide the therapeutic effects to the user as described herein. For example, one or more components of the strap system 105 (e.g., the first strap 110, the second strap 150, the first attachment region 140, and the second attachment region 160) may be integrated into, combined with, or attached to the glove 100 in a variety of configurations. By way of further example, the central portion 115 of the first strap 110 may be disposed in several different manners at the region of the glove 100 where the thumb element 120 of the glove 100 merges with the first finger element 130 of the glove 100. For convenience, this region may be referred to hereinafter as the cradle 118 (or alternatively a saddle region).

Figure 8:
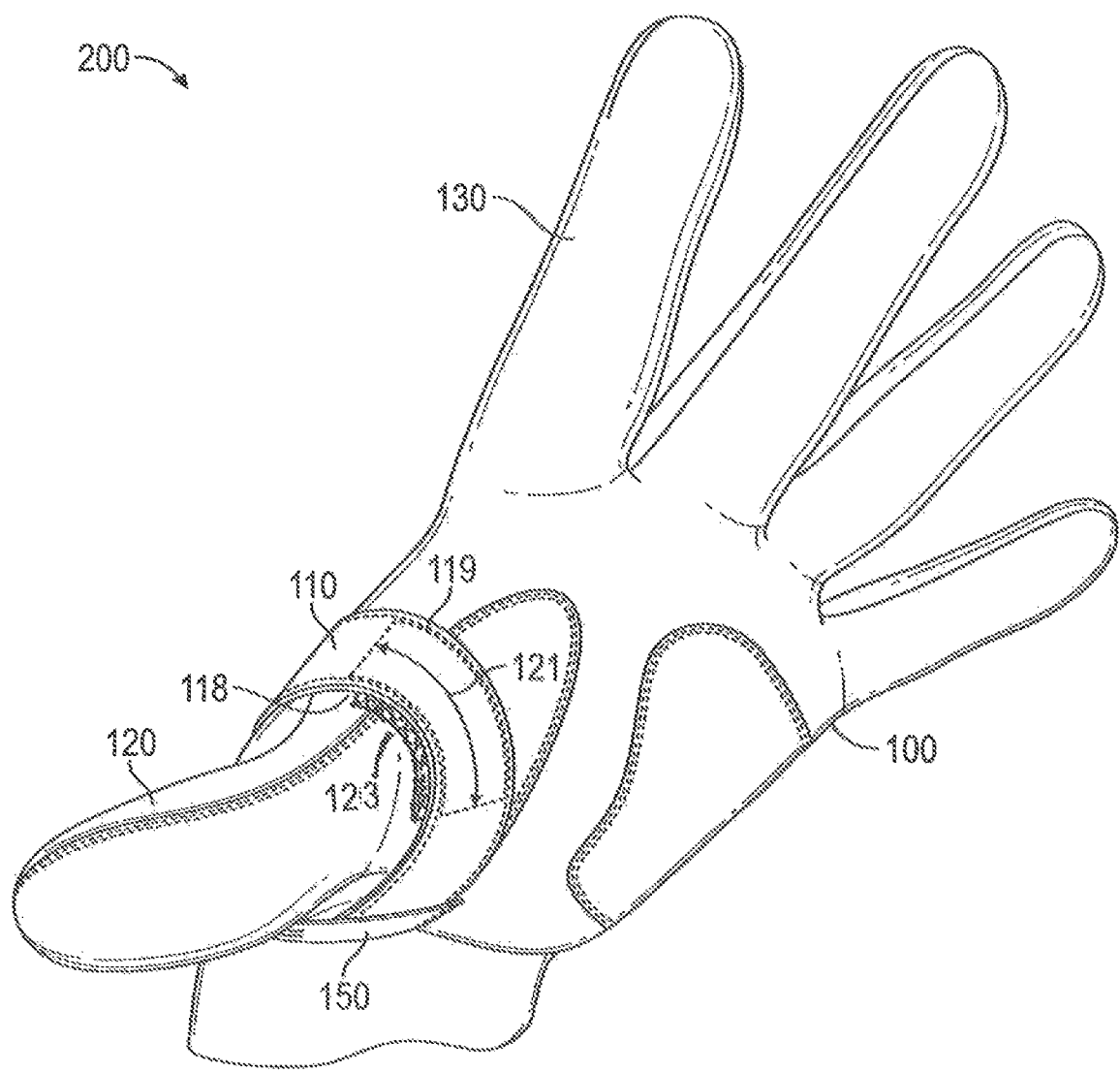
FIG. 8 is a view of a cradle area of a thumb brace according to an embodiment of the present disclosure.

FIG. 8 illustrates one manner in which the first strap 110 may be disposed at the cradle 118. In this embodiment, the first strap 110 is a single piece of material the central portion 115 of which may be fixedly attached to the exterior of the glove 100 at the cradle 118 by stitching 119, forming a contact region 121 between underside 113 of the first strap 110 and the cradle 118 of glove 100. In alternative embodiments, the first strap 110 is a single piece of material the central portion 115 of which may be fixedly attached to the exterior of the glove 100 at the cradle 118 by adhesive (e.g., glue) in contact region 121, a combination of adhesive and stitching in contact region 121, or other such known attachment means. In alternative embodiments, the first strap 110 is a single piece of material the central portion 115 of which may be removably attached to the exterior of the glove 100 at the cradle 118 by a temporary attachment such as a hook and loop fastener, or other such known attachment means. For example, contact region 121 may comprise a strip of hook fabric (e.g., having a width about equal to the width of the first strap 110) stitched to the outer surface of cradle 118. The first strap 110 may then be adjustably attached to the glove 100 by selectively engaging and disengaging the strip of hook fabric with the loop fabric located on the underside 113 of the first strap 110. Removably attaching the first strap 110 to the cradle 118 by hook and loop fastener allows the user to adjust the length of the ends 111 and 112 of the first strap 110 by varying the placement of the central portion 115 on the contact region 121, or otherwise adjust the positioning, comfort, or support provided by the thumb brace 200.

In an alternative embodiment, contact region 121 does not comprise an attachment means, that is the first strap 110 is in contact with the cradle 118 during use but is not otherwise fixedly or removably attached to the glove 100 by stitching, adhesive, hook and loop fastener, etc. For example, first end 111 of a loose (i.e., not otherwise attached) first strap 110 may be attached to the first attachment region 140 (e.g., via hook and loop fastener or other fastener such as a snap such as the type that are sometimes included on golf gloves for holding a removable ball marker); the first strap 110 stretched and wrapped around the thumb and into contact with the cradle 118; and the second end 112 of the first strap 110 attached to the first attachment region 140 to provide the attachment configuration for the first strap 110 as shown in FIG. 4 and described in detail herein. In another embodiment, contact region 121 does not comprise an attachment means and either first end 111 or second end 112 of the first strap 110 is fixedly attached proximate the first attachment region 140, such as via stitching such as that shown in FIG. 7 with respect to first end 151 of second strap 150. For example, first end 111 of first strap 110 may be fixedly attached to the first attachment region 140 via stitching and/or adhesive; the first strap 110 stretched and wrapped around the thumb and into contact with the cradle 118; and the second end 112 of the first strap 110 attached to the first attachment region 140 to provide the attachment configuration for the first strap 110 as shown in FIG. 4 and described in detail herein. In the embodiments of FIG. 8, the entirety of the first strap 110 is disposed on the exterior of the glove 100.

Figure 9:
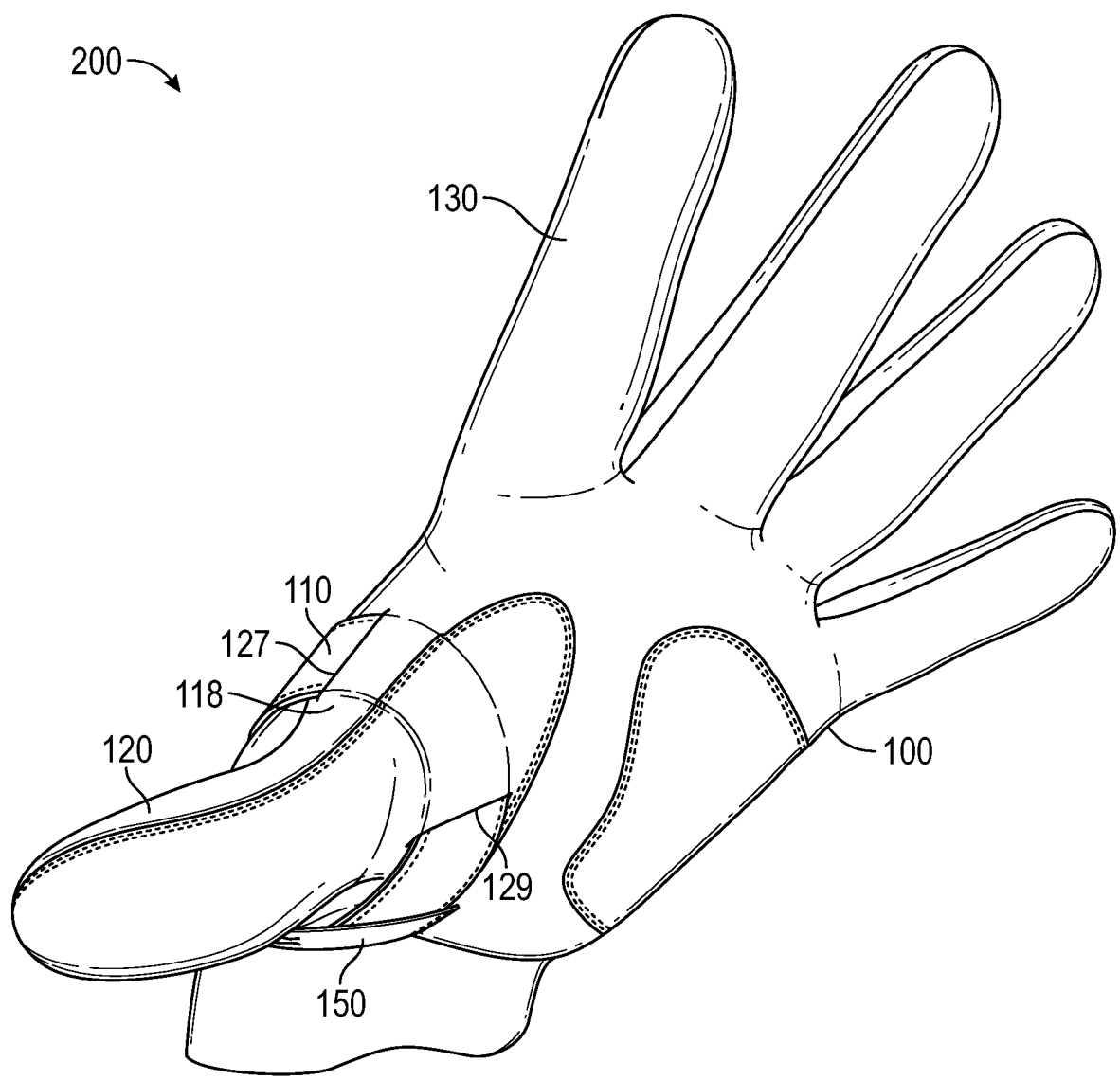
FIG. 9 is another view of a cradle area of a thumb brace according to an embodiment of the present disclosure.

FIG. 9 illustrates another manner in which the first strap 110 may be disposed at the cradle 118. In this embodiment, the first strap 110 is again a single piece of material, but the entirety of the first strap 110 is not disposed on the exterior of the glove 100, as in the embodiment of FIG. 8. Instead, a central portion 115 of the first strap 110 passes through the interior of the glove 100 beneath the cradle 118 (i.e., on the inside glove surface of the cradle 118). The first end 111 of the first strap 110 emerges from the interior of the glove 100 on the dorsal side of the cradle 118 via an opening such as slit 127, and the second end 112 of the first strap 110 emerges from the interior of the glove 100 on the palmar side of the cradle via an opening such as slit 129. The first strap 110 may optionally be attached to the glove 100 near the slits 127 and 129 where each end emerges from the interior of the glove 100. Alternatively or additionally, the portion of the first strap 110 that passes through the interior of the glove 100 may be attached to the interior of the glove, thus forming an interior contact region analogous to contact region 121. Again, the attachment may occur by stitching, adhesive, or other known attachment means. As another alternative, the central portion 115 of the first strap 110 may not be attached to the glove 100 near the cradle 118 but instead may be allowed to at least partially slide in and out of slits 127 and 129 and through the interior of the glove 100 under the cradle 118, for example similar to a belt passing through a belt loop. In this alternative, attachment of the first strap 110 to the glove 100 occurs only by ends 111 and 112 in contact with the first attachment region 140, and the central portion 115 of the first strap 110 is held in place by the portion disposed on the interior glove surface between the slits 127 and 129. For example, first end 111 of first strap 110 may be attached to the first attachment region 140 (e.g., via hook and loop fastener or other fastener such as a snap such as the type that are sometimes included on golf gloves for holding a removable ball marker), and the first strap 110 is free to slide through the slits 127 and 129 during attachment of the first end 111; the second end 112 of the first strap 110 may be stretched with the central portion 115 passing through an interior surface of the glove between slits 127 and 129; and the second end 112 of the first strap 110 attached to the first attachment region 140 to provide the attachment configuration for the first strap 110 as shown in FIG. 4 and described in detail herein. Configuring the first strap 110 in the manner of FIG. 9 may reduce the profile of the glove 100 (e.g., the palm of the glove 100 has a substantially uniform surface without any ridges or edges associated with the first strap 110 to interfere with gripping an article such as a golf club), and thereby improve the feel and mobility of the hand of a wearer of the glove 100 as compared to the configuration of FIG. 8.

Figure 10:
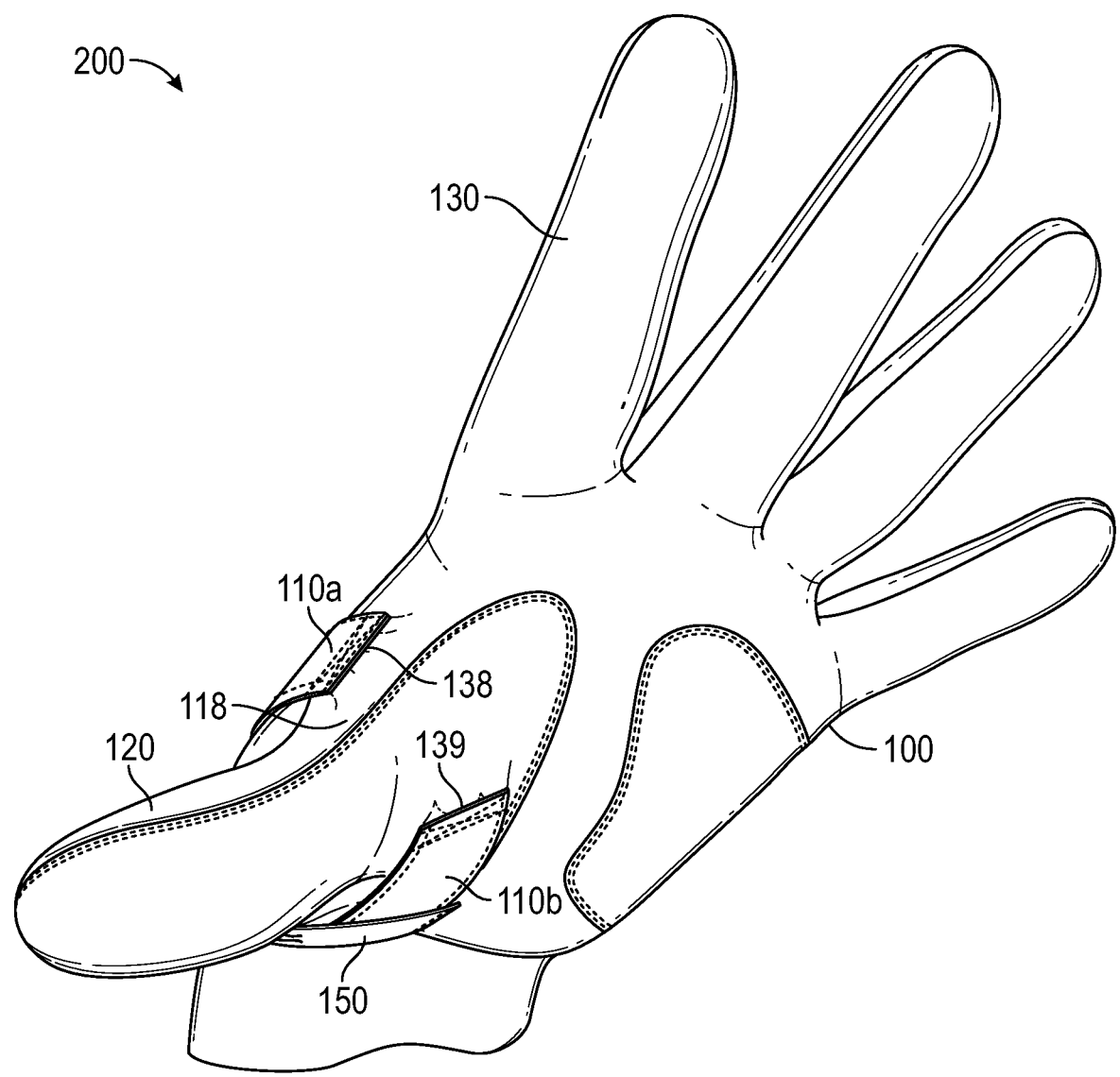
FIG. 10 is another view of a cradle area of a thumb brace according to an embodiment of the present disclosure.

FIG. 10 illustrates another manner in which the first strap 110 may be disposed at the cradle 118. In this embodiment, the first strap 110 is discontinuous and comprises two pieces or sections of material, 110a and 110b. First section 110a

(having first end 111) extends from the glove 100 on the dorsal side of the cradle 118, and the second section 110b (having second end 112) extends from the glove 100 on the palmar side of the cradle 118. Edge portion 138 of first section 110a and edge portion 139 of second section 110b may be fixedly attached to the exterior of the glove 100 near the regions where the ends extend from the glove 100. Once again, the attachment may occur by stitching, gluing, or other known attachment means. Alternatively, the glove 100 may be manufactured such that one end of each of the two sections 110a and 110b of the first strap 110 is connected as an integral component of the glove 100 (e.g., integral, strap attachment tabs extending outward from the material, e.g., leather, forming the palm of the glove) near the cradle region 118 where the sections 110a and 110b extend from the glove 100. The first end 111 of the first strap 110 may be stretched taut and attached to the first attachment region 140 (e.g., via hook and loop fastener or other fastener), and the second end 112 of the first strap 110 may be stretched taut and attached to the first attachment region 140 to provide the attachment configuration for the first strap 110 as shown in FIG. 4 and described in detail herein. Tautly stretching and attaching ends 111 and 112 correspondingly pulls the cradle 118 portion of the glove taut against the user's hand, which lifts or extends the distal portion 30 of the thumb metacarpal bone 10, for example as shown by reference arrow 1020 in FIG. 13. Tautly stretching the two sections 110a and 110b from the regions of connection near the cradle to the first attachment region 140 in such manner may place stress on the regions of connection and thereby increase the likelihood of tearing in the region of the cradle 118. In an embodiment, to reduce the likelihood of such tearing, a reinforcing material may be added to the region of the cradle 118. The reinforcing material may be added to exterior of the cradle region, the interior of the cradle region, or both. Configuring the first strap 110 in the manner of FIG. 10 may also reduce the profile and/or thickness of the glove 100 (e.g., the palm of the glove 100 has a substantially uniform surface without any ridges, edges, or changes in thickness associated with the first strap 110 to interfere with gripping an article such as a golf club) as compared to the configurations of FIGS. 8 and 9, and thereby improve the feel and mobility of the hand of a wearer of the glove 100 as compared to the configurations of FIGS. 8 and 9.

FIG. 11 illustrates an outline of the thumb brace 200 comprising glove 100 superimposed over a dorsal view of the bones of a left human hand. In this view, the loose ends of the first strap 110 and the second strap 150 have not been attached to the glove 100 at the first attachment region 140 or the second attachment region 160. Without support from the first strap 110 and the second strap 150, the thumb metacarpal bone 10 has subluxed in the manner of a patient with arthritis in the CMC joint 25. This subluxation can be seen from the fact that the proximal end 5 of the thumb metacarpal bone 10 is not parallel with the distal end 22 of the trapezium bone 20. Thus, the thumb metacarpal bone 10 interfaces with the trapezium bone 20 only in the small region 70.

Figure 12:
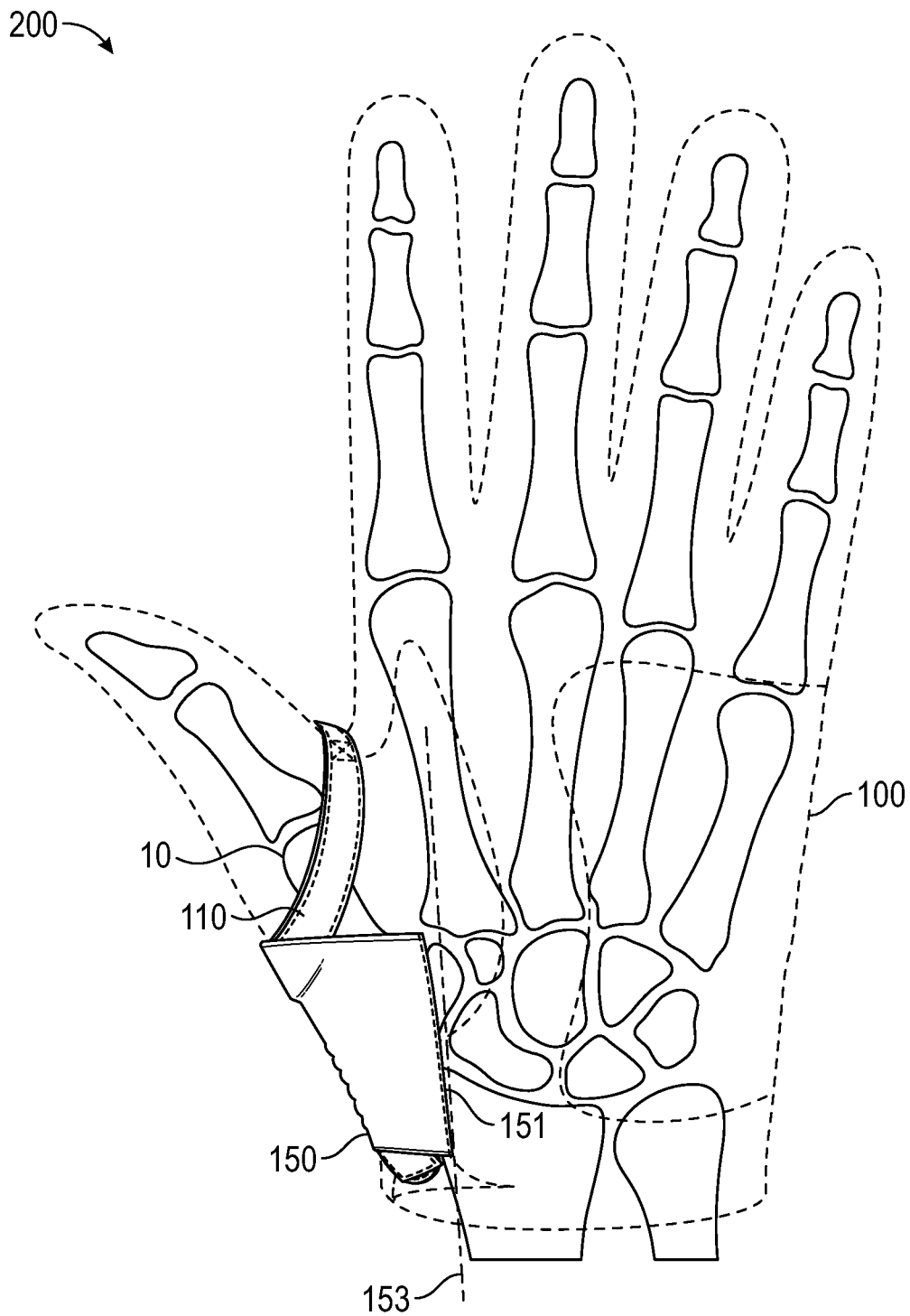
FIG. 12 illustrates an outline of a thumb brace superimposed over a palmar view of the bones of a left human hand according to an embodiment of the present disclosure.

FIG. 12 illustrates an outline of the thumb brace 200 comprising glove 100 superimposed over a palmar view of the bones of a left human hand. In this view, the loose ends of the first strap 110 and the second strap 150 have been attached to the glove 100 at the first attachment region 140 and the second attachment region 160, respectively, in the manner described herein.

FIG. 13 illustrates the results of attaching the first strap 110 and the second strap 150 to the glove 100 in the manner shown in FIGS. 4, 5, 6, 7, and 12 and described in detail herein. That is, the first end 111 of the first strap 110 and the second end 112 of the first strap 110 have been attached to the glove 100 above the proximal portion 5 of the thumb metacarpal bone 10, as shown in FIGS. 11 and 13. In addition, the second strap 150 has been attached to the glove 100 across a dorsal proximal portion of the thumb metacarpal bone 10. From FIG. 13, it can be seen that, compared with the subluxation depicted in FIG. 1 and FIG. 11, the proximal portion 5 of the thumb metacarpal bone 10 has moved in the direction indicated by reference arrow 1010 and that dorsal subluxation of the proximal portion 5 of the thumb metacarpal bone 10 has thus been reduced. It can further be seen that, compared with the subluxation depicted in FIG. 1 and FIG. 11, the distal portion 30 of the thumb metacarpal bone 10 has moved in the direction indicated by reference arrow 1020 and that the distal portion 30 of the thumb metacarpal bone 10 has thus become extended. Thus, the thumb metacarpal bone 10 and the trapezium bone 20 have become properly aligned, and the interface between the thumb metacarpal bone 10 and the trapezium bone 20 has returned to its preferred configuration, wherein the facing ends of the thumb metacarpal bone 10 and the trapezium bone 20 are substantially parallel with one another and share loads across the entire interface of the CMC joint 25.

Figure 14:
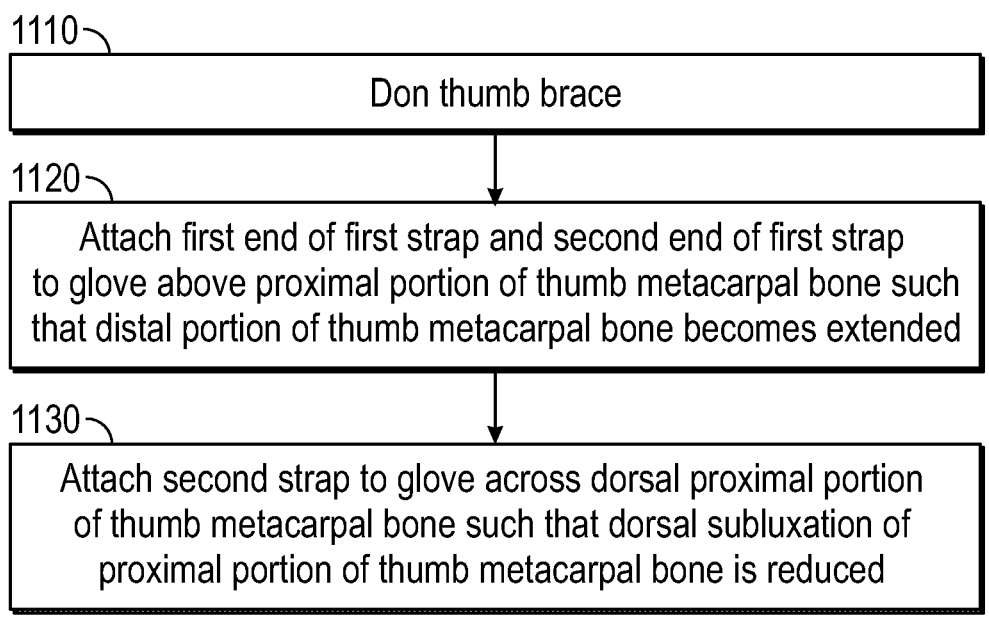
FIG. 14 is a flowchart of a method for aligning a thumb metacarpal bone with a trapezium bone according to an embodiment of the present disclosure.

FIG. 14 is a flowchart illustrating a method for aligning a thumb metacarpal bone with a trapezium bone via use of one or more embodiments of the thumb brace described in the present disclosure. At block 1110, a thumb brace is donned. The thumb brace may comprises a glove, a first strap, and a second strap as described herein. At block 1120, a first end of the first strap and a second end of the first strap are attached to the glove above a proximal portion of the thumb metacarpal bone such that a distal portion of the thumb metacarpal bone becomes extended. At block 1130, the second strap is attached to the glove across a dorsal proximal portion of the thumb metacarpal bone such that dorsal subluxation of the proximal portion of the thumb metacarpal bone is reduced.

The method of FIG. 14 may further comprise extending the first end of the first strap from a first region of attachment of a central portion of the first strap at a region of the glove where a thumb element of the glove merges with a first finger element of the glove, around one of a palmar region of the glove and a dorsal region of the glove, to a second region of attachment above the proximal portion of the thumb metacarpal bone. The method may further comprise extending the second end of the first strap from the first region of attachment, around the other of the palmar region of the glove and the dorsal region of the glove, to the second region of attachment.

The method of FIG. 14 may further comprise extending an end of the second strap remote from a third region of attachment of the second strap at a ventral side of a wrist region of the glove, across the dorsal proximal portion of the thumb metacarpal bone, to a fourth region of attachment above the dorsal side of the wrist region of the glove. The method may further comprise attaching the end of the second strap to the fourth region of attachment.

More generally, the thumb brace may be said to comprise a first means or mechanism for extending a distal portion of a thumb metacarpal bone and a second means or mechanism for reducing dorsal subluxation of a proximal portion of the thumb metacarpal bone, said first and second means being supported by a glove as described herein.

In one embodiment, the first means or mechanism may be a single piece of material that is substantially longer than wide and is attached to or integral with the exterior of the glove in a region of the glove where a thumb element of the glove merges with a first finger element of the glove. In another embodiment, the first means or mechanism may also be a single piece of material that is substantially longer than wide, and a central portion of the elastic material may pass through an interior space of the glove. A first end portion of the elastic material may emerge from the interior space of the glove on the dorsal side of the region of the glove where the thumb element of the glove merges with the first finger element of the glove. A second end portion of the elastic material may emerge from the interior space of the glove on the palmar side of the region of the glove where the thumb element of the glove merges with the first finger element of the glove.

In another embodiment, the first means or mechanism may be two pieces of material, each of which is substantially longer than wide. A first of the two pieces may extend from the exterior of the glove on a dorsal side of the region of the glove where the thumb element of the glove merges with the first finger element of the glove. A second of the two pieces may extend from the exterior of the glove on a palmar side of the region of the glove where the thumb element of the glove merges with the first finger element of the glove.

In any of the above embodiments, a first end of the first means or mechanism may be configured to pass over a palmar region of the glove or a dorsal region of the glove and attach to the glove above a dorsal portion of the thumb metacarpal bone. A second end of the first means or mechanism may be configured to pass over the other of the palmar region of the glove or the dorsal region of the glove and attach to the glove above the first end.

In any of the above embodiments, a first end of the second means or mechanism may be attached to or integral with the glove at a ventral side of a wrist region of the glove. A second end of the second means or mechanism may be configured to pass over the proximal portion of the thumb metacarpal bone and a portion of the radius bone of a wearer of the glove and attach to a dorsal side of the wrist region of the glove. The second end of the second means or mechanism, when attached to the dorsal side of the wrist region of the glove, may cover at least a portion of the first means or mechanism.

In the above embodiments, the first means or mechanism and the second means or mechanism may be elastic straps, the ends of which may be stretched to a preferred position to achieve the alignment of the thumb metacarpal bone as described above. In other embodiments, the first means or mechanism and the second means or mechanism are not elastic. Instead, the lengths and orientations of the first means or mechanism and the second means or mechanism and the positions and sizes of the regions of the attachment of the first means or mechanism and the second means or mechanism to the glove may be such that the attachment may occur only within a narrow range of orientations. The alignment of the thumb metacarpal bone described above may occur when the attachment occurs within this narrow range of orientations.

As mentioned above, any or all of the finger elements of the glove 100 may be absent, and/or portions of any or all of the finger elements may be absent. Such a fully or partially fingerless version of the glove 100 may be useful for hunting, fishing, woodworking, gardening, needlework, and other activities where fine control of one or more fingers may be needed and where alignment and stabilization of the thumb as described herein may be desirable. Also, it should be understood that the glove 100 may provide the above described benefits when the wearer is not engaged in any such specific activities. That is, a wearer may choose to wear the glove 100 for comfort, stability and/or pain relief while engaged in routine daily activities instead of or in addition to wearing the glove 100 while engaged in a specific sport, hobby or pastime.

In an embodiment, thumb brace 200 further comprises one or more pads associated with glove 100 to cushion one or more areas of a hand of a user of the brace from an impact force. For example, one or more areas internal to the glove, one or more areas external to the glove, or both may comprise a pad or other cushioning material effective to cushion, absorb, or otherwise lessen an impact force (and thus potential pain associated therewith) to the hand of a user wearing the brace. In particular, a user suffering from CMC arthritis may have a tender or sore CMC joint that is sensitive to an impact force such as bumping, jamming, etc. that may be incurred during an activity (e.g., golfing) that the user is engaged in while wearing the brace. Accordingly, in an aspect one or more pads may be placed internal and/or external to the glove 100 (e.g., attached to and/or integral with an interior and/or external surface of the glove 100) and located proximate the CMC joint of a user of the brace to cushion, absorb, or otherwise lessen an impact force to the CMC joint of the user, thereby aiding in the comfort and/or pain relief of the user engaged in an activity (e.g., golf) while wearing the brace 200. All or a portion of the pad may be attached to the glove, for example stitched to the glove (e.g., directly or indirectly), releasably attached to the glove (e.g., via hook and loop fastener), contained within a pocket or pouch integral with the glove, etc. The pad may comprise any suitable material effective to cushion, absorb, or otherwise lessen an impact force to the user (e.g., the CMC joint of a user), for example foam (e.g., viscoelastic polyurethane foam), natural or synthetic rubber, silicon rubber, etc. In an aspect, the pad may comprise a cover, for example a fabric or material similar to a material used in glove 100. In an aspect, the pad comprises a leather cover that is similar to or the same as one or more leather components of the glove 100, for example similar to or the same as synthetic or natural leather (e.g., cabretta leather) used in a golf glove. In a further aspect, end 112 of first strap 110 may be attached to the first attachment region 140 and/or attached to the cover and/or glove, for example via stitching.

Figure 16:
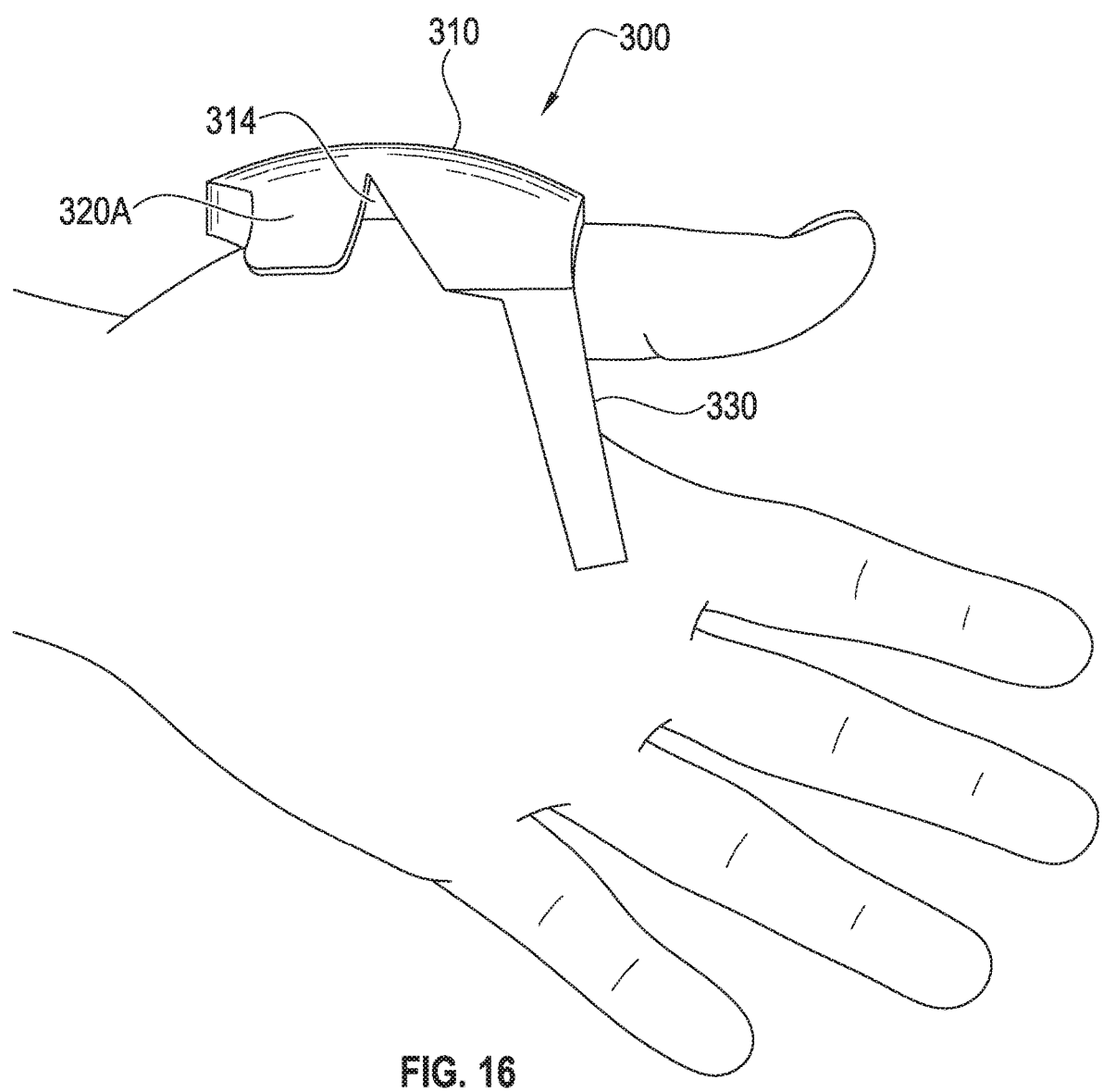
FIGS. 16-17 are perspective views showing the positioning of pad 300 with respect to a thumb and associated CMC joint of a left hand of a user of a thumb brace comprising the pad 300.
Figure 17:
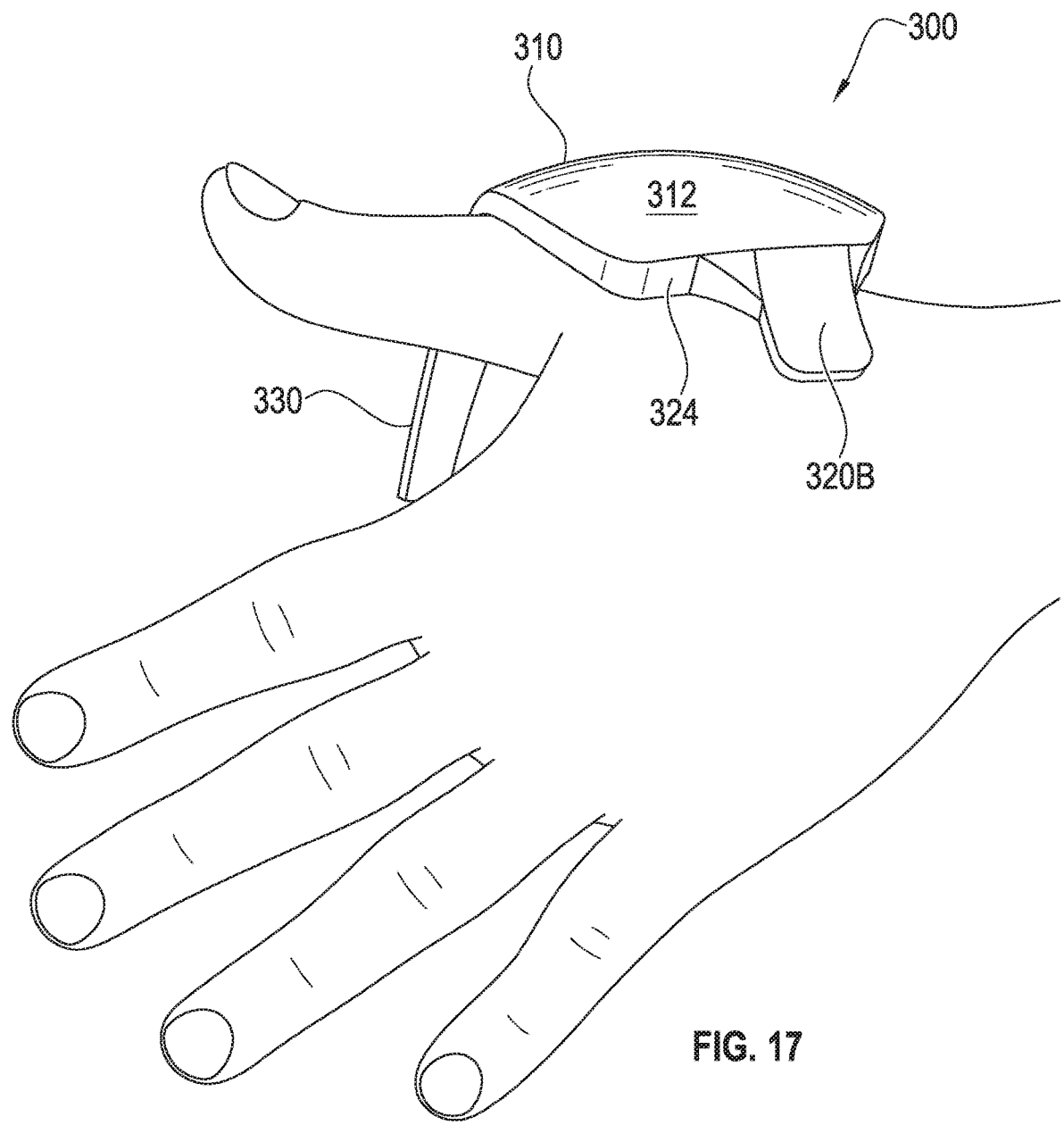
Figure 18:
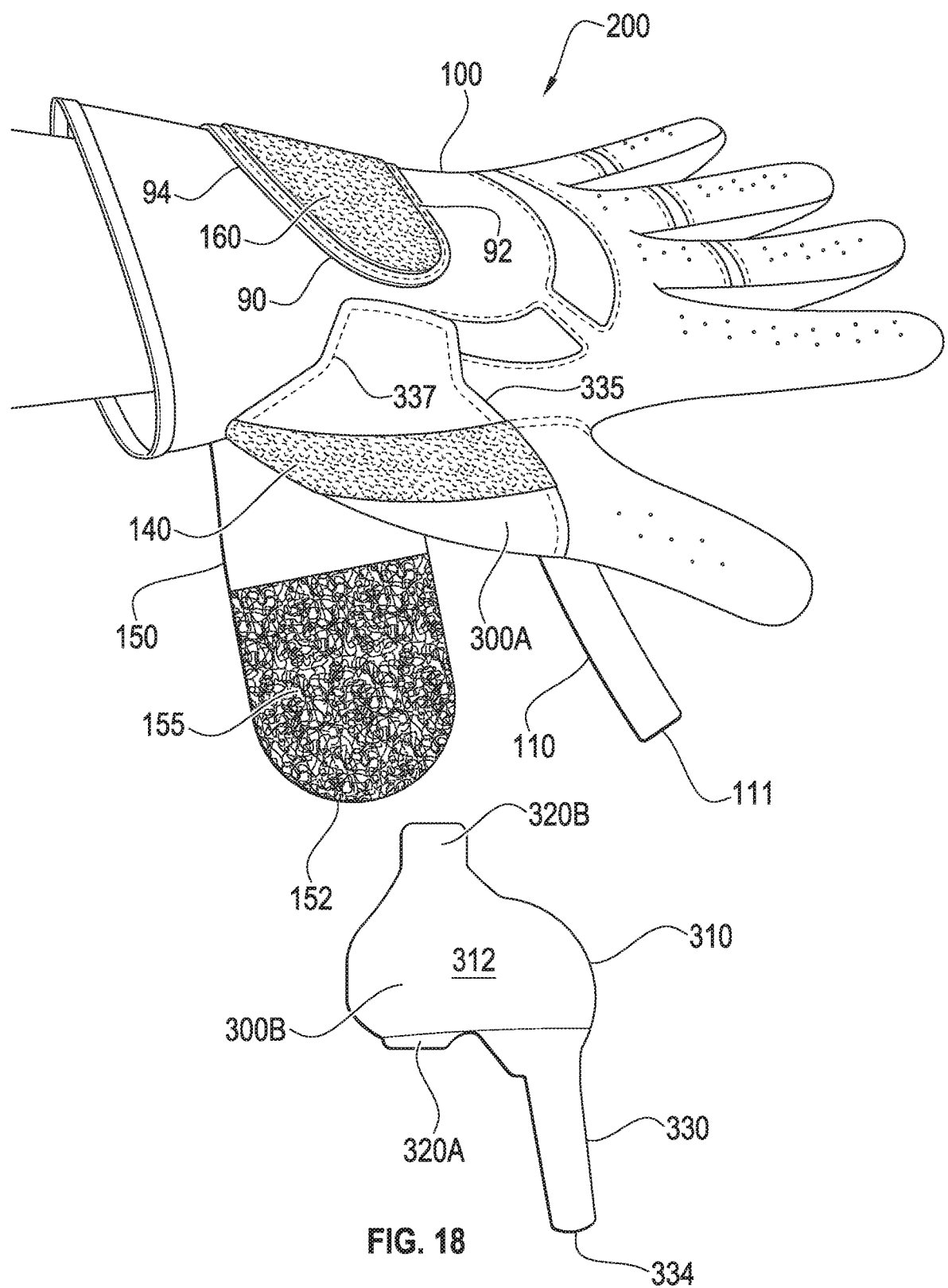
FIGS. 18-20 are perspective views of an embodiment of a thumb brace 200 further comprising a pad, for example pad 300 in accordance with FIGS. 15-17.

Referring to FIGS. 15-18, an embodiment of a pad 300 is illustrated. Pad 300 comprises a cushioning portion 310 which may have an upper surface 312 and a lower surface 314. The cushioning portion 310 may be of any suitable size and shape to provide a desired cushioning effect, for example sized to effectively cushion an area proximate to CMC joint 25 of FIGS. 1, 11, and 13. In an aspect, the cushioning portion 310 may have a generally oval, ellipse, capsule (or stadium), or egg shape or cross-section when viewed from the top as shown in FIG. 18 or viewed from the bottom.

Referring to FIGS. 15-18, in an aspect the pad 300 can further comprise one or more tabs 320A/B, for example attached to or integral with cushioning portion 310. Tabs 320A/B (e.g., front tab 320A and back tab 320B) may be of any suitable size or shape, for example square or rectangular. As shown in FIGS. 15-18, tabs 320A/B may be of a generally rectangular shape having an edge attached to or integral with one or more edges of cushioning portion 310. As shown in FIGS. 15-18, at least one edge of front tab 320A can be attached to or formed integral with and extend outward from front edge 322 of cushioning portion 310, and at least one edge of back tab 320B can be attached to or formed integral with and extend outward from back edge 324 of cushioning portion 310. Tabs 320A/B may provide additional cushioning area and/or may provide an attachment surface for attaching the pad 300 to the glove 100, for example via stitching.

Referring to FIGS. 15-18, in an aspect the pad 300 can further comprise an additional elongated tab 330, which may also be referred to as a reinforcing or reinforcement member, a reinforcing or reinforcement portion, a reinforcing or reinforcement tab, or the like. Reinforcement member 330 may be of any suitable size or shape, for example elongated and/or rectangular. As shown in FIGS. 15-18, reinforcement member 330 may be of a generally elongated, rectangular shape having an edge attached to or integral with one or more edges of cushioning portion 310. As shown in FIGS. 15-18, at least one edge (e.g., top edge 332) of reinforcement member 330 can be attached to or formed integral with and extend outward and/or downward from front edge 322 of cushioning portion 310 and having a bottom edge 334. Reinforcement member 330 may provide additional cushioning area, an additional attachment surface for attaching the pad 300 to the glove 100, and/or may reinforce or otherwise supplement one or more additional components of the strap system 105 (e.g., reinforce or otherwise supplement the first strap 110 designed to lift or extend the distal end 30 of the thumb metacarpal bone 10 and/or reinforce or otherwise supplement the second strap 150 designed to reduce the dorsal subluxation at the proximal end 5 of the thumb metacarpal bone 10). In an aspect, the reinforcement member 330 comprises an elastomeric material (e.g., molded silicon rubber) and is attached to all or a portion of first strap 110, and thus is effective to provide a tension spring/elastomeric force upon being stretched (e.g., stretched concurrent with stretching of elastic first strap 110).

The components of pad 300, e.g., cushioning portion 310, tabs 320 A/B, and reinforcement member 330) can be separate components that are coupled together to form pad 300 and/or the components of pad 300, e.g., cushioning portion 310, tabs 320 A/B, and reinforcement member 330) can be integral with each other and comprise a unitary, monolithic structure (e.g., a single part or structure molded from silicone rubber). In an aspect, the components of pad 300, e.g., cushioning portion 310, tabs 320 A/B, and reinforcement member 330) comprise a unitary, integral structure formed from (e.g., comprising) CAST-A-MOLD platinum cured RTV silicone rubber.

Figure 15:
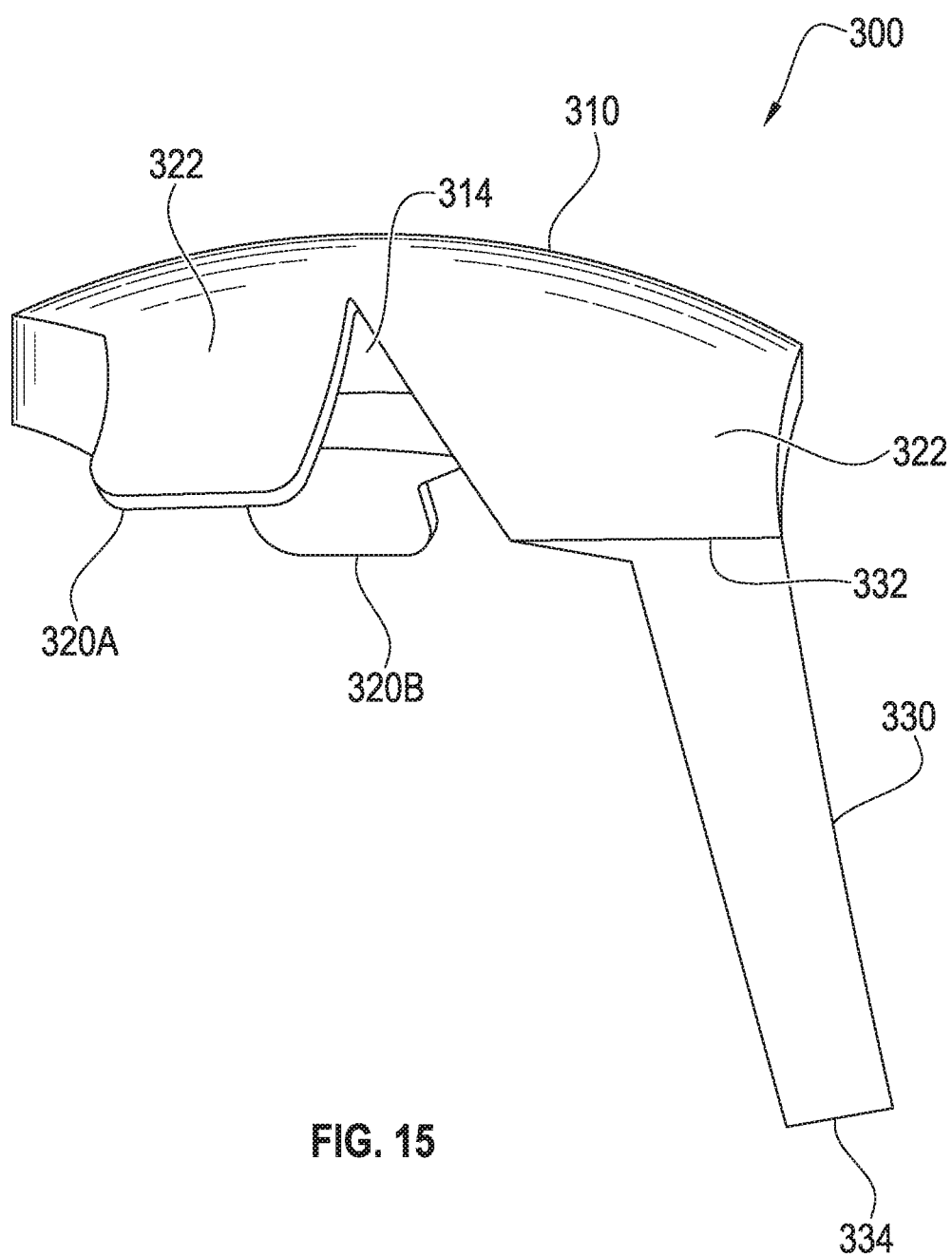
FIG. 15 illustrates an embodiment of a pad 300.
Figure 19:
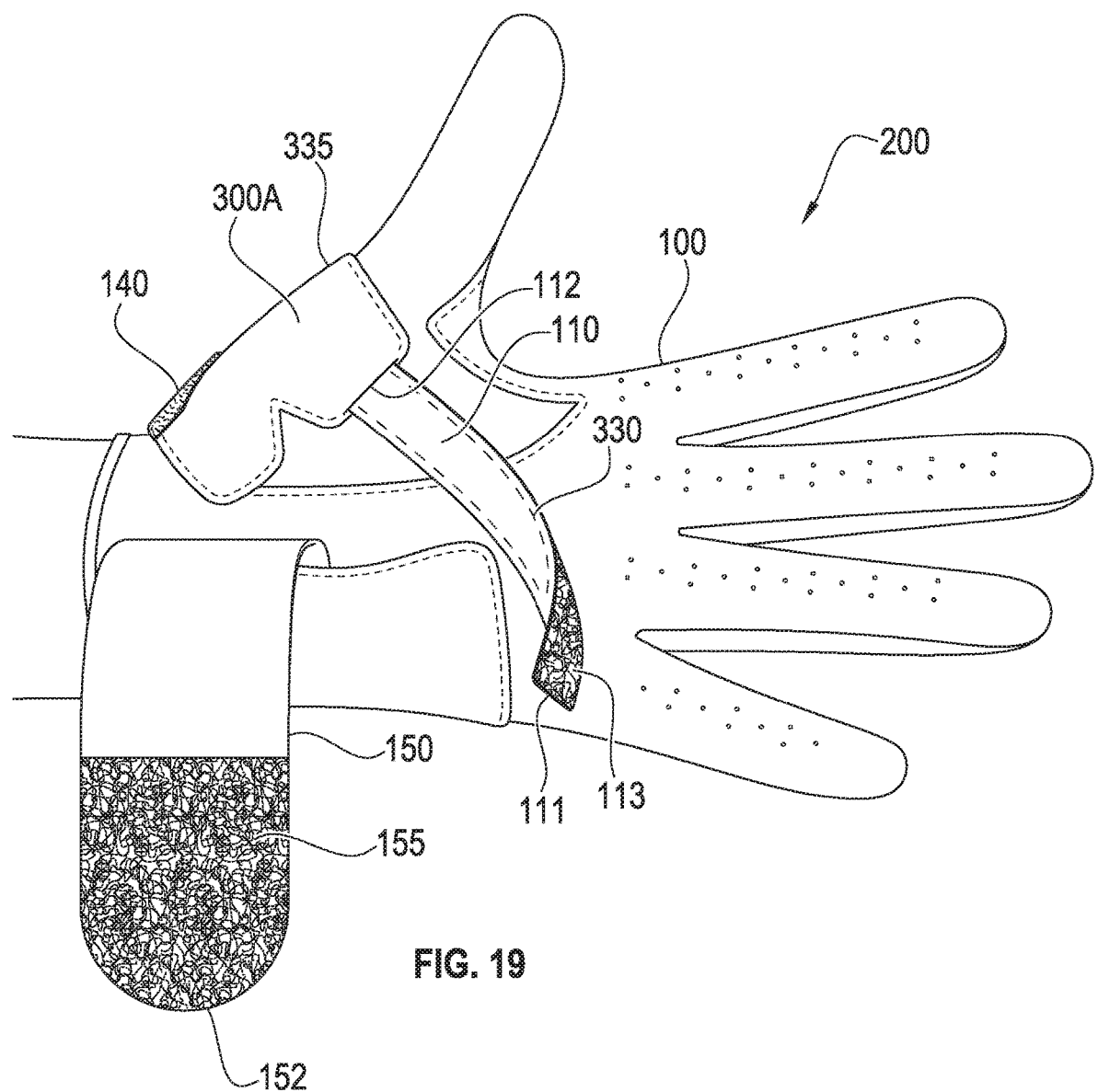
Figure 20:
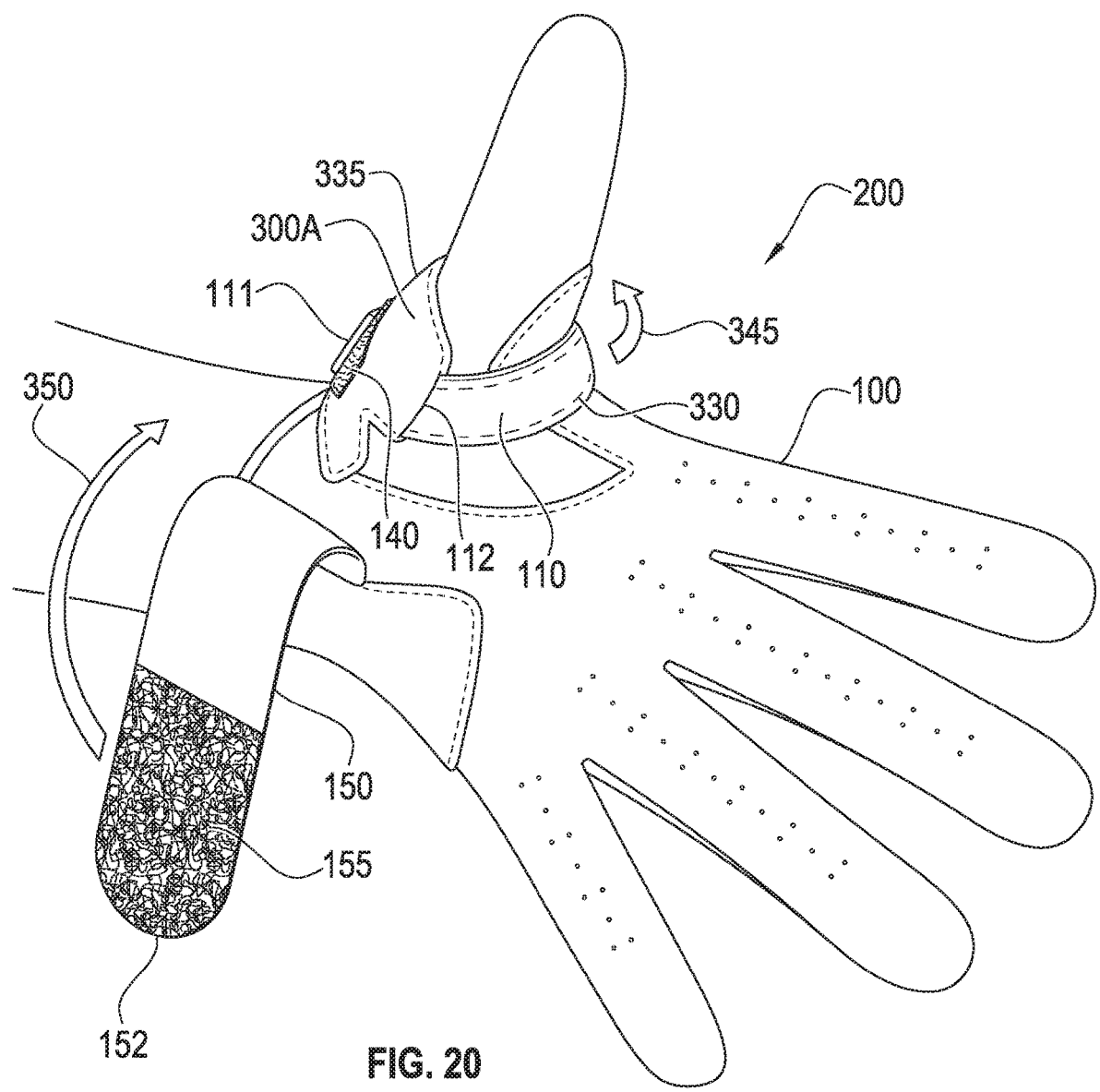

FIGS. 16 (front view) and 17 (back view) illustrate an embodiment of the positioning of the pad 300 with respect to a thumb and associated CMC joint of a user. It should be understood that the pad 300 is shown in isolation for clarity in FIGS. 16 and 17, but that pad 300 can be added as a component of thumb brace 200 as is described in further detail herein (e.g., as shown in FIGS. 18-20). As shown in FIGS. 15-17, bottom surface 314 of cushioning portion 310 of pad 300 can be cupped or concave to correspond to the curvature of the base of the thumb when placed proximate thereto. Accordingly, in an aspect, the cushioning portion 310 of pad 300 has an arched or semi-circular cross-sectional shape. The cupped or concave cushioning portion 310 (and associated arched or semi-circular cross-sectional shape) allow the pad 300 to conform to the back of the thumb and fit close to the CMC joint without interfering with the grip of a user as shown in FIGS. 16 and 17, for example when included as a component in thumb brace 200 (e.g., as shown in FIGS. 18-20).

FIGS. 18-20 are various perspective views of an embodiment of thumb brace 200 further comprising a pad, for example pad 300 in accordance with FIGS. 15-17. In the embodiment shown in FIGS. 18-20, thumb brace 200 comprises a glove 100, a pad 300A, and a strap system 105 including a first strap 110 designed to lift or extend the distal end 30 of the thumb metacarpal bone 10 and a second strap 150 designed to reduce the dorsal subluxation at the proximal end 5 of the thumb metacarpal bone 10 at the CMC joint 25. As shown in FIGS. 18-20, pad 300A is at least partially enclosed or covered by a cover 335, for example a fabric and/or leather cover. The cover 335 can be sized and shaped to accommodate all or a portion of each component of the pad 300, for example cushioning portion 310, tabs 320A/B, and reinforcement member 330. The cover 335 can be attached (e.g., stitched) to the glove 100 as shown by stitching 337 and thereby attach the pad to the outer surface of glove 100. In an aspect, pad 300A is attached (e.g., stitched) to the glove 100 at a location proximate to, the same as, and/or encompassing the location of the first attachment region 140 as described in more detail herein. In an aspect, the first attachment region 140 (e.g., comprising a hook or loop portion of a fastener) can be collocated such that the first attachment region 140 is on an outer surface of cover 335 enclosing pad 300A (see, e.g., FIGS. 18 and 19). Also shown in FIG. 18 is an unattached, uncovered pad 300B which is orientated similar to covered pad 300A that is attached (e.g., stitched) to glove 100, thereby providing a further spatial reference for the position and orientation of covered pad 300A. In a further aspect, end 112 of first strap 110 may be attached to the first attachment region 140 and/or attached to the cover 335 and/or glove 100, for example via stitching as shown in FIG. 19.

As shown in FIG. 19, reinforcement member 330 (shown in ghosting via dashed lines) may be positioned along all or a portion of first strap 110 to reinforce and support first strap 110. As shown in FIG. 19, reinforcement member 330 and first strap 110 can be about the same width, reinforcement member 330 can extend a portion of the length of first strap 110, and reinforcement member 330 and first strap 110 can be attached to each other, for example via adhesive, stitching, and/or within a common cover (e.g., cover 335). As shown in FIG. 19, a portion of strap 110 can extend beyond end 334 of reinforcement member 330 such that at least a portion of the underside 113 of the first strap 110 adjacent the end 111 comprises a portion of the hook and loop fastener, that is, the underside 113 of end 111 of the first strap 110 can attach to and detach from the first attachment region 140 of glove 100.

FIGS. 18-20 illustrate a sequence of a user (e.g., person) donning (e.g., putting on or wearing) a thumb brace 200 according to an embodiment of the present disclosure as described in more detail herein. The sequence of FIGS. 18-20 are shown in the context of the left hand of a user, with the understanding that the thumb brace can be worn on either or both hands of a user. As described previously herein, thumb brace 200 comprises a glove 100 and a strap system 105 including a first strap 110 designed to lift or extend the distal end 30 of the thumb metacarpal bone 10 and a second strap 150 designed to reduce the dorsal subluxation at the proximal end 5 of the thumb metacarpal bone 10 at the CMC joint 25.

Referring to FIG. 18, a user inserts his or her hand into the glove 100, and the glove may be secured to the hand of the user. For example, glove may have an adjustable cuff, for example an elastic cuff or an adjustably sized cuff as provided by a tab closure such as flap 90 on the back of the glove (i.e., dorsal or back side of the hand) that may be opened or closed by way of a fastener such as a hook and loop fasteners, zipper, etc. The flap 90 has an external face or surface 92 that is typically a smooth fabric (often adorned by a manufacturer's logo) in a standard glove (but, in contrast, embodiments according to the present disclosure may further comprise second attachment region 160 on external flap surface 92, as described in detail herein). The flap 90 typically further comprises an interior face or surface comprising a first portion (e.g., loop portion) of the hook and loop fastener. The flap 90 overlaps a portion 94 of the back of the glove having disposed thereon the opposite portion of the hook and loop fastener (e.g., the hook portion) such that the glove flap 90 may be adjustably closed and opened by engaging and disengaging, respectively, the hook and loop fastener portions associated with the flap 90 and overlapped portion 94 of the back of the glove.

Referring to FIGS. 18-20, the strap system 105 further comprises a first strap 110, a second strap 150, a first attachment region 140, and a second attachment region 160. After a user places the glove 100 on his or her hand as shown in FIG. 18, the first strap 110 is stretched and wrapped around the thumb (e.g., between the index finger and the thumb) and connected to the first attachment region 140 as shown in FIG. 20. For example, first strap 110 is stretched and positioned around the thumb (e.g., between the index finger and the thumb as shown by reference arrow 345), and end 111 of first strap 110 is attached to the first attachment region 140 (which may attached to cover 335 and positioned proximate or atop the pad 300A). The end 112 of first strap 110 may likewise be attached to the first attachment region 140, or may be attached to the cover 335 and/or glove 100, for example via stitching as shown in FIGS. 19-20. Stretching the first strap 110 likewise stretches the reinforcement member 330 that is attached to first strap 110 as shown in FIGS. 19-20. The stretched first strap 110 and/or the stretched reinforcement member 330 provide a force in the direction of reference arrow 1020 to the thumb metacarpal bone such that a distal portion of the thumb metacarpal bone becomes extended as shown in FIG. 13 and described in more detail with reference thereto.

After the first strap 110 is positioned as shown in FIG. 20, the second strap 150 is stretched and positioned (as indicated by reference arrow 350) across the back of the wrist adjacent the base of the thumb and attached to second attachment region 160 as shown in FIG. 6. At least a portion of the underside 155 of the second strap 150 adjacent the second end 152 comprises a portion of a hook and loop fastener that attaches to (and can likewise detach from) the second attachment region 160 of glove 100. The stretched second strap 150 provides a force in the direction of reference arrow 1010 to the thumb metacarpal bone such that dorsal subluxation of the proximal portion of the thumb metacarpal bone is reduced as shown in FIG. 13 and described in more detail with reference thereto. Upon donning of the glove 100 and attaching the first strap 110 and the second strap 150 of the strap system 105, the thumb brace 200 supports the CMC joint (as described in detail herein with reference to FIG. 13) and pad 300 further cushions the CMC joint from impact forces while not interfering with griping a tool (e.g., a golf club, tennis racket, hammer, etc.).

Additional Embodiments Group I

A first embodiment that is a thumb brace comprising a glove having a thumb portion disposed between a palm side and a back side and comprising a first attachment region positioned adjacent a base of the thumb portion and adjacent to and/or along a midline where the palm side and back side meet and a second attachment region positioned on the back side of the glove; a first elastic strap having a first end, a mid-portion, and a second end, wherein the mid-portion is disposed within a cradle of the glove between the thumb portion and an index finger portion of the glove, the first end is releasably attached to the first attachment region, and the second end is releasably attached to the first attachment region, whereby the first strap extends a distal end of a thumb metacarpal bone of a user of the brace; and a second elastic strap having a first end, a mid-portion, and a second end, wherein the first end is attached to the palm side of the glove and the second end is releasably attached to the second attachment region, whereby the second strap reduces a proximal end of a thumb metacarpal bone of a user of the brace.

A second embodiment that is the thumb brace of the first embodiment wherein the glove has a flap on the back side providing an adjustably sized cuff, and wherein the second attachment region is located on a back surface of the flap.

A third embodiment that is the thumb brace of the first and second embodiments wherein the first strap is attached to the glove proximate the cradle of the glove.

A fourth embodiment that is the thumb brace of the first through third embodiments wherein the first strap is releasably attached to the glove.

A fifth embodiment that is the thumb brace of the first through third embodiments wherein the first strap is stitched to the glove.

A sixth embodiment that is the thumb brace of the fifth embodiment wherein the first strap is continuous from the first end to the second end, wherein the entire length of the first strap is disposed on the exterior of the glove, and wherein the first strap is stitched to the glove proximate the mid-portion of the first strap.

A seventh embodiment that is the thumb brace of fifth embodiment wherein the first strap is discontinuous having a first section including the first end and a second section including the second end, wherein the first section is stitched to the cradle opposite the first end, and wherein the second section is stitched to the cradle opposite the second end.

An eighth embodiment that is the thumb brace of the first through forth embodiments wherein the first strap is continuous from the first end to the second end, the cradle further comprises a first slit and a second slit, and all or a portion of the mid-portion of the first strap is slidably disposed inside the glove between the first and second slits.

A ninth embodiment that is the thumb brace of the first through eighth embodiments wherein the first and second ends of the first strap are releasably connected to the first attachment region by a first hook and loop fastener and wherein the second end of the second strap is releasably connected to the second attachment region by a second hook and loop fastener.

A tenth embodiment that is the thumb brace of the second through ninth embodiments wherein the flap is releasably connected to the back side of the glove by a third hook and loop fastener.

An eleventh embodiment that is the thumb brace of the first through tenth embodiments wherein the glove is a golf glove.

A twelfth embodiment that is the thumb brace of the first through eleventh embodiments wherein at least a portion of the mid-portion of the second strap passes over the first strap.

A thirteenth embodiment that is the thumb brace of the first through twelfth embodiments wherein at least a portion of the mid-portion of the second strap passes over the first and second ends of the first strap.

A fourteenth embodiment that is the thumb brace of the first through thirteenth embodiments wherein the second end of the first strap overlaps the first end of the first strap.

A fifteenth embodiment that is a thumb brace comprising: a glove comprising first, second, and third hook and loop fasteners, wherein the first hook and loop fastener provides an adjustable cuff opening for the glove; the second hook and loop fastener connects first and second ends of a first elastic strap positioned on the glove to extend a distal end of a thumb metacarpal bone of a user of the glove; and the third hook and loop fastener connects the second end of a second elastic strap positioned on the glove to reduce a proximal end of a thumb metacarpal bone of a user of the glove.

A sixteenth embodiment that is the thumb brace of the fifteenth embodiment wherein a first end of the second strap is stitched to the glove.

A seventeenth embodiment that is the thumb brace of the fifteenth or sixteenth embodiments wherein a mid-portion of the first strap is stitched to the glove, and wherein the first strap is continuous or discontinuous.

An eighteenth embodiment that is the thumb brace of the fifteenth or sixteenth embodiments further comprising a fourth hook and loop fastener connecting a mid-portion of the first strap to a cradle of the glove.

A nineteenth embodiment that is the thumb brace of the fifteenth through eighteenth embodiments wherein the glove is a golf glove.

A twentieth embodiment that is a method of using a thumb brace comprising a glove and a strap system, the method comprising: placing the glove on a hand experiencing subluxation of the thumb metacarpal bone; extending a distal end of the thumb metacarpal bone by releasably connecting a first elastic strap of the strapping system to a first attachment region on the glove; and reducing a proximal end of the thumb metacarpal bone by releasably connecting a second elastic strap to a second attachment region of the glove.

A twenty-first embodiment that is the method of the twentieth embodiment wherein placing the glove on the hand further comprises releasably attaching a flap portion of an adjustable cuff of the glove to the back of the glove, and wherein a back surface of the flap comprises the second attachment region of the glove.

A twenty-second embodiment that is the method of twentieth or twenty-first embodiments wherein the thumb brace comprises: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove, the first end is releasably attached to the first attachment region, and the second end is releasably attached to the first attachment region, whereby the first strap extends a distal end of a thumb metacarpal bone of a user of the brace; and a second elastic strap having a first end, a mid-portion, and a second end, wherein the first end is attached to the palm side of the glove and the second end is releasably attached to the second attachment region, whereby the second strap reduces a proximal end of a thumb metacarpal bone of a user of the brace.

A twenty-third embodiment that is the method of the twentieth or twenty-first embodiments wherein the thumb brace comprises: a glove comprising first, second, and third hook and loop fasteners, wherein the first hook and loop fastener provides an adjustable cuff opening for the glove; the second hook and loop fastener connects first and second ends of a first elastic strap positioned on the glove to extend a distal end of a thumb metacarpal bone of a user of the glove; and the third hook and loop fastener connects the second end of a second elastic strap positioned on the glove to reduce a proximal end of a thumb metacarpal bone of a user of the glove.

A twenty-fourth embodiment that is the method of the twentieth through twenty-third embodiments wherein the glove is a golf glove.

A twenty-fifth embodiment that is a method of making a thumb brace comprising, providing a glove and attaching a strap system of the type disclosed herein to the glove in accordance with the various embodiments and figures disclosed herein. In such embodiment, hook and loop fastener components (e.g. sections of fabric comprising the hook or loop component) are attached (e.g., stitched) to the ends of the first and second straps as disclosed herein, and the complementary component of the hook and loop fastener is attached to the glove in the attachment regions disclosed herein. The first and second straps may be attached to the glove as described herein, for example by stitching.

A twenty-sixth embodiment that is a method of treating a subject experiencing thumb carpometacarpal joint arthritis comprising providing a thumb brace according to the first through nineteenth embodiments to the subject with instructions comprising a sequence for releasably attaching the first and second straps to the first and second contact regions, respectively.

A twenty-seventh embodiment that is a packaged article for commerce comprising the thumb brace of according to the first through nineteenth embodiments and instructions comprising a sequence for releasably attaching the first and second straps to the first and second contact regions, respectively.

A twenty-eighth embodiment that is a method of treating a subject experiencing thumb carpometacarpal joint arthritis comprising extending a distal end of the thumb metacarpal bone via a first force provided by an a first elastic strap positioned proximate or adjacent the distal end; and reducing a proximal end of the thumb metacarpal bone via a second force provided by a second elastic strap positioned proximate or adjacent the proximal end, wherein the first force and the second force are substantially opposite in direction such that a rotational force is provided on the metacarpal bone effective to relieve on or more indications of CMJ arthritis. In such embodiment, the first and second forces may be provided by the thumb brace according to the first through nineteenth embodiments.

A twenty-ninth embodiment that is a glove, for example a golf glove, comprising first, second, and third hook and loop fasteners, wherein the first hook and loop fastener provides an adjustable cuff opening; the second hook and loop fastener connects first and second ends of a first elastic strap positioned on the glove to extend a distal end of a thumb metacarpal bone of a user of the glove; and the third hook and loop fastener connects the second end of a second elastic strap positioned on the glove to reduce a proximal end of a thumb metacarpal bone of a user of the glove.

A thirtieth embodiment that is a glove, for example a golf glove, having a thumb portion disposed between a palm side and a back side, and comprising: a first contact region positioned adjacent a base of the thumb along a midline where the palm side and back side meet and a second contact region positioned on the back side of the glove; a first elastic strap having a first end, a mid-portion, and a second end, wherein the mid-portion is disposed within a cradle of the glove between the thumb portion and an index finger portion of the glove, the first end is releasably attached to the first contact region, and the second end is releasably attached to the first contact region, whereby the first strap extends a distal end of a thumb metacarpal bone of a user of the brace; and a second elastic strap having a first end, a mid-portion, and a second end, wherein the first end is attached to the palm side of the glove and the second end is releasably attached to the second contact region, whereby the second strap reduces a proximal end of a thumb metacarpal bone of a user of the brace.

A thirty-first embodiment that is a glove, for example a golf glove, comprising: a first mechanism for extending a distal portion of a thumb metacarpal bone; and a second mechanism for reducing dorsal subluxation of a proximal portion of the thumb metacarpal bone.

A thirty-second embodiment that is the glove of the thirty-first embodiment, wherein the first mechanism comprises one of: (i) a single piece of elastic material, substantially longer than wide, attached to the exterior of the glove in a region of the glove where a thumb element of the glove merges with a first finger element of the glove; (ii) a single piece of elastic material, substantially longer than wide, wherein a central portion of the elastic material passes through an interior space of the glove, wherein a first end portion of the elastic material emerges from the interior space of the glove to the exterior of the glove on the dorsal side of the region of the glove where the thumb element of the glove merges with the first finger element of the glove, and wherein a second end portion of the elastic material emerges from the interior space of the glove to the exterior of the glove on the palmar side of the region of the glove where the thumb element of the glove merges with the first finger element of the glove; or (iii) two pieces of elastic material, each substantially longer than wide, wherein a first of the pieces extends from the exterior of the glove on a dorsal side of the region of the glove where the thumb element of the glove merges with the first finger element of the glove, and wherein a second of the pieces extends from the exterior of the glove on a palmar side of the region of the glove where the thumb element of the glove merges with the first finger element of the glove.

A thirty-third embodiment that is the glove of the thirty-first or thirty-second embodiments, wherein a first end of the first mechanism is configured to pass over one of a palmar region of the glove and a dorsal region of the glove and attach to the glove above a dorsal portion of the thumb metacarpal bone, and wherein a second end of the first mechanism is configured to pass over the other of the palmar region of the glove and the dorsal region of the glove and attach to the glove above the first end.

A thirty-fourth embodiment that is the glove of the thirty-third embodiment, wherein the first end and the second end are of such a length, and wherein a region of the attachment of the first end and the second end to the glove is in such a position above the dorsal portion of the thumb metacarpal bone, that extension of the distal portion of the thumb metacarpal bone is capable of occurring when the attachment occurs.

A thirty-fifth embodiment that is the glove of the thirty-third and thirty-fourth embodiments, wherein a region of the attachment of the first end and the second end to the glove comprises: a first indicator indicating a preferred position of the first end when the first end is attached; and a second indicator indicating a preferred position of the second end when the second end is attached.

A thirty-sixth embodiment that is the glove of the thirty-second through thirty-fifth embodiments, wherein, when the first mechanism comprises two pieces of elastic material, the region of the glove where the thumb element of the glove merges with the first finger element of the glove is reinforced such that the likelihood of tearing of the region of the glove where the thumb element of the glove merges with the first finger element of the glove is reduced.

A thirty-seventh embodiment that is the glove of the thirty-third through thirty-sixth embodiments, wherein the attachment of the first end and the second end to the glove occurs by one of: a hook and loop fastening system; a snap fastening system; or a button fastening system.

A thirty-eight embodiment that is the glove of the thirty-first through thirty-seventh embodiments, wherein a first end of the second mechanism is attached to the glove at a ventral side of a wrist region of the glove, and wherein a second end of the second mechanism is configured to pass over the proximal portion of the thumb metacarpal bone and a radius bone of a wearer of the glove and attach to a dorsal side of the wrist region of the glove.

A thirty-ninth embodiment that is the glove of the thirty-eighth embodiment, wherein the second end of the second mechanism, when attached to the dorsal side of the wrist region of the glove, covers at least a portion of the first mechanism.

A fortieth embodiment that is the glove of thirty-eighth or thirty-ninth embodiment, wherein the attachment of the second end of the second mechanism to the dorsal side of the wrist region of the glove occurs by one of: a hook and loop fastening system; a snap fastening system; or a button fastening system.

A forty-first embodiment that is a glove, for example a golf glove, comprising: a first elastic strapping mechanism configured to exert pressure on a palmar region of a distal portion of a thumb metacarpal bone; and a second elastic strapping mechanism configured to exert pressure on a dorsal region of a proximal portion of the thumb metacarpal bone.

A forty-second embodiment that is a glove, for example a golf glove, comprising: a first strapping mechanism configured to be capable of exerting pressure on a distal portion of a thumb metacarpal bone, such that the distal portion of the thumb metacarpal bone moves in a manner characteristic of extending the thumb metacarpal bone; and a second strapping mechanism configured to be capable of exerting pressure on a proximal portion of the thumb metacarpal bone, such that the proximal portion of the thumb metacarpal bone moves in a direction opposite to the movement of the distal portion of the thumb metacarpal bone.

A forty-third embodiment that is a method for aligning a thumb metacarpal bone with a trapezium bone, the method comprising: donning a glove, for example a golf glove, wherein the glove comprises a first strap and a second strap; attaching a first end of the first strap and a second end of the first strap to the glove above a proximal portion of the thumb metacarpal bone such that a distal portion of the thumb metacarpal bone becomes extended; and attaching the second strap to the glove across a dorsal proximal portion of the thumb metacarpal bone such that dorsal subluxation of the proximal portion of the thumb metacarpal bone is reduced.

A forty-fourth embodiment that is the method of the forty-third embodiment, further comprising: extending the first end of the first strap from a first region of attachment of a central portion of the first strap at a region of the glove where a thumb element of the glove merges with a first finger element of the glove, around one of a palmar region of the glove and a dorsal region of the glove, to a second region of attachment above the proximal portion of the thumb metacarpal bone; and extending the second end of the first strap from the first region of attachment, around the other of the palmar region of the glove and the dorsal region of the glove, to the second region of attachment.

A forty-fifth embodiment that is the method of the forty-third or forty-fourth embodiment, further comprising: extending an end of the second strap remote from a third region of attachment of the second strap at a ventral side of a wrist region of the glove, across the dorsal proximal portion of the thumb metacarpal bone, to a fourth region of attachment above the dorsal side of the wrist region of the glove; and attaching the end of the second strap to the fourth region of attachment.

Additional Embodiments Group II

A first embodiment that is a thumb brace comprising: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove, wherein the first strap is attached via stitching to the glove, wherein the first strap is continuous from the first end to the second end, wherein a length of the first strap is disposed on the exterior of the glove, wherein the first end, the second end, or both are releasably attachable to the first attachment region, and wherein the first strap extends from the cradle of the glove and wraps around both sides of the thumb portion of the glove such that the first strap extends a distal end of a gloved thumb metacarpal bone of a gloved hand of a user of the brace; a second elastic strap having a first end, a mid-portion, and a second end, wherein the first end is attached to the palm side of the glove and the second end is releasably attachable to the second attachment region, wherein the second strap reduces a proximal end of a gloved thumb metacarpal bone of a gloved hand of a user of the brace; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of the user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A second embodiment that is the thumb brace of the first embodiment wherein the glove has a flap on the back side providing an adjustably sized cuff, and wherein the second attachment region is located on a back surface of the flap.

A third embodiment that is the thumb brace of the first and second embodiments wherein the first strap is attached to the glove proximate the cradle of the glove.

A fourth embodiment that is the thumb brace of any of the first through third embodiments wherein at least a portion of the mid-portion of the second strap passes over the first strap.

A fifth embodiment that is the thumb brace of any of the first through fourth embodiments wherein the second end of the first strap overlaps the first end of the first strap.

A sixth embodiment that is the thumb brace of any of the first through fifth embodiments wherein the glove is a golf glove.

A seventh embodiment that is a thumb brace comprising: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove and the first end, the second end, or both are releasably attached to the first attachment region, wherein the first strap extends a distal end of a gloved thumb metacarpal bone of a gloved hand of a user of the brace; a second elastic strap having a first end, a mid-portion, and a second end, wherein the first end is attached to the palm side of the glove and the second end is releasably attached to the second attachment region, wherein the second strap reduces a proximal end of a gloved thumb metacarpal bone of a gloved hand of a user of the brace; and a pad (e.g., a pad as shown in FIGS. 15-21 and further described herein by reference to FIGS. 22-48) attached to the glove and positioned proximate (e.g., below) the second attachment region and adjacent the base of the thumb portion on the back side of the glove such that the pad cushions a CMC joint of the user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

An eighth embodiment that is the thumb brace of seventh embodiment wherein the glove has a flap on the back side providing an adjustably sized cuff, and wherein the second attachment region is located on a back surface of the flap.

A ninth embodiment that is the thumb brace of seventh or eighth embodiments wherein the first strap is attached to the glove proximate the cradle of the glove.

A tenth embodiment that is the thumb brace of any of the seventh through ninth embodiments wherein the first strap is stitched to the glove.

An eleventh embodiment that is the thumb brace of any of the seventh through tenth embodiments wherein the first strap is continuous from the first end to the second end, wherein a length of the first strap is disposed on an exterior of the glove, and wherein the first strap is stitched to the glove.

A twelfth embodiment that is the thumb brace of any of the seventh through eleventh embodiments wherein the glove is a golf glove.

A thirteenth embodiment that is the thumb brace of any of the seventh through twelfth embodiments wherein at least a portion of the mid-portion of the second strap passes over the first strap.

A fourteenth embodiment that is the thumb brace of any of the seventh through thirteenth embodiments wherein the second end of the first strap overlaps the first end of the first strap.

A fifteenth embodiment that is a thumb brace comprising: a glove comprising first, second, and third hook and loop fasteners, wherein the first hook and loop fastener provides an adjustable cuff opening for the glove; the second hook and loop fastener connects first, second, or both ends of a first elastic strap positioned on the glove to extend a distal end of a gloved thumb metacarpal bone of a gloved hand of a user of the glove; and the third hook and loop fastener connects the second end of a second elastic strap positioned on the glove to reduce a proximal end of a gloved thumb metacarpal bone of a gloved hand of a user of the glove; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of the user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A sixteenth embodiment that is the thumb brace of the fifteenth embodiment wherein a first end of the second strap is stitched to the glove.

A seventeenth embodiment that is the thumb brace of the fifteenth or sixteenth embodiments wherein the first strap is stitched to the glove, and wherein the first strap is continuous or discontinuous.

An eighteenth embodiment that is the thumb brace of any of the fifteenth through seventeenth embodiments wherein at least a portion of the mid-portion of the second strap passes over the first strap.

A nineteenth embodiment that is the thumb brace of any of the fifteenth through eighteenth embodiments wherein the second end of the first strap overlaps the first end of the first strap.

A twentieth embodiment that is the thumb brace of any of the fifteenth through nineteenth embodiments wherein the glove is a golf glove.

A twenty-first embodiment that is a thumb brace comprising: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove, wherein the first strap is attached via stitching to the glove proximate the cradle of the glove, wherein the first strap is continuous from the first end to the second end, wherein the entire length of the first strap is disposed on the exterior of the glove, wherein the first strap is stitched to the glove proximate the mid-portion of the first strap, wherein the first end is releasably attachable to the first attachment region and the second end is releasably attachable to the first attachment region, and wherein the first strap extends from the cradle of the glove and wraps around both sides of the thumb portion of the glove when the first and second ends of the first strap are releasably attached to the first attachment region, whereby the first strap extends a distal end of a thumb metacarpal bone of a user of the brace; a second elastic strap having a first end, a mid-portion, and a second end, wherein the first end is attached to the palm side of the glove and the second end is releasably attachable to the second attachment region, whereby the second strap reduces a proximal end of a thumb metacarpal bone of a user of the brace; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of a user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A twenty-second embodiment that is a method of using a thumb brace comprising a glove and a strap system, the method comprising: placing the glove on a hand experiencing subluxation of the thumb metacarpal bone; extending a distal end of the thumb metacarpal bone by releasably connecting a first elastic strap of the strapping system to a first attachment region on the glove; and reducing a proximal end of the thumb metacarpal bone by releasably connecting a second elastic strap to a second attachment region of the glove, wherein the thumb brace comprises: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove, wherein the first strap is attached via stitching to the glove proximate the cradle of the glove, wherein the first strap is continuous from the first end to the second end, wherein the entire length of the first strap is disposed on the exterior of the glove, wherein the first strap is stitched to the glove proximate the mid-portion of the first strap, wherein the first end is releasably attachable to the first attachment region and the second end is releasably attachable to the first attachment region, and wherein the first strap extends from the cradle of the glove and wraps around both sides of the thumb portion of the glove when the first and second ends of the first strap are releasably attached to the first attachment region, whereby the first strap extends a distal end of a thumb metacarpal bone of a user of the brace; a second elastic strap having a first end, a mid-portion, and a second end, wherein the first end is attached to the palm side of the glove and the second end is releasably attachable to the second attachment region, whereby the second strap reduces a proximal end of a thumb metacarpal bone of a user of the brace; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of a user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A twenty-third embodiment that is a thumb brace comprising: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove, the first end is releasably attached to the first attachment region, and the second end is releasably attached to the first attachment region, wherein the first strap extends a distal end of a gloved thumb metacarpal bone of a gloved hand of a user of the brace; a second elastic strap having a first end, a mid-portion, and a second end, wherein the first end is attached to the palm side of the glove and the second end is releasably attached to the second attachment region, wherein the second strap reduces a proximal end of a gloved thumb metacarpal bone of a gloved hand of a user of the brace; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of the user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A twenty-fourth embodiment that is a thumb brace comprising: a glove comprising first, second, and third hook and loop fasteners, wherein the first hook and loop fastener provides an adjustable cuff opening for the glove; the second hook and loop fastener connects first and second ends of a first elastic strap positioned on the glove to extend a distal end of a gloved thumb metacarpal bone of a gloved hand of a user of the glove; the third hook and loop fastener connects the second end of a second elastic strap positioned on the glove to reduce a proximal end of a gloved thumb metacarpal bone of a gloved hand of a user of the glove; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of the user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A twenty-fifth embodiment that is a method of using a thumb brace comprising a glove and a strap system, the method comprising: placing the glove on a hand experiencing subluxation of the thumb metacarpal bone; extending a distal end of the gloved thumb metacarpal bone of the gloved hand by releasably connecting a first elastic strap of the strapping system to a first attachment region on the glove; and reducing a proximal end of the gloved thumb metacarpal bone of the gloved hand by releasably connecting a second elastic strap to a second attachment region of the glove, wherein the glove further comprises a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of a user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A twenty-sixth embodiment that is a thumb brace comprising: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove, wherein the first strap is attached via stitching to the glove, wherein the first strap is continuous from the first end to the second end, wherein a length of the first strap is disposed on the exterior of the glove, wherein the first end, the second end, or both are releasably attachable to the first attachment region, and wherein the first strap extends from the cradle of the glove and wraps around both sides of the thumb portion of the glove such that the first strap extends a distal end of a gloved thumb metacarpal bone of a gloved hand of a user of the brace; a second elastic strap having a first end, a mid-portion, and a second end, wherein the first end is attached to the palm side of the glove and the second end is releasably attachable to the second attachment region, wherein the second strap reduces a proximal end of a gloved thumb metacarpal bone of a gloved hand of a user of the brace; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of the user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A twenty-seventh embodiment that is a thumb brace comprising: a glove having a thumb portion disposed between a palm side and a back side and comprising a first attachment region positioned adjacent a base of the thumb portion and a second attachment region positioned on the back side of the glove; a first elastic strap having a first end, a mid-portion, and a second end, wherein the mid-portion is disposed within a cradle of the glove between the thumb portion and an index finger portion of the glove and the first end, the second end, or both are releasably attached to the first attachment region, wherein the first strap extends a distal end of a gloved thumb metacarpal bone of a gloved hand of a user of the brace; a second elastic strap having a first end, a mid-portion, and a second end, wherein the first end is attached to the palm side of the glove and the second end is releasably attached to the second attachment region, wherein the second strap reduces a proximal end of a gloved thumb metacarpal bone of a gloved hand of a user of the brace; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of a user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

A twenty-eighth embodiment that is a thumb brace comprising: a glove comprising first, second, and third hook and loop fasteners, wherein the first hook and loop fastener provides an adjustable cuff opening for the glove; the second hook and loop fastener connects first, second, or both ends of a first elastic strap positioned on the glove to extend a distal end of a gloved thumb metacarpal bone of a gloved hand of a user of the glove; the third hook and loop fastener connects the second end of a second elastic strap positioned on the glove to reduce a proximal end of a gloved thumb metacarpal bone of a gloved hand of a user of the glove; and a pad (e.g., a pad as shown in FIGS. 15-17 and further described herein by reference to FIGS. 18-20) attached to the glove and positioned proximate (e.g., below) the second attachment region and adjacent the base of the thumb portion on the back side of the glove such that the pad cushions a CMC joint of the user of the brace from impact, wherein the pad may optionally be enclosed by a cover material (e.g., fabric and/or leather), wherein the cover material may be attached to (e.g., stitched) the glove, and wherein the pad can further comprise a reinforcement member that is attached to at least a portion of the first elastic strap.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A thumb brace comprising:
   a glove having a thumb portion disposed between a palm side and a back side and comprising a first attachment region positioned adjacent a base of the thumb portion and a second attachment region positioned on the back side of the glove;
   a first elastic strap having a first end, a mid-portion, and a second end, wherein the mid-portion is disposed within a cradle of the glove between the thumb portion and an index finger portion of the glove and the first end, the second end, or both are releasably attached to the first attachment region, wherein the first strap is configured to extend a distal end of a gloved thumb metacarpal bone of a gloved hand of a user of the brace; and
   a second elastic strap having a first end, a mid-portion, and a second end, wherein the first end is attached to the palm side of the glove and the second end is releasably attachable to the second attachment region, wherein the second strap is configured to reduce a dorsal subluxation at a proximal end of the gloved thumb metacarpal bone of the gloved hand of the user of the brace; and
   a pad attached to the glove and positioned proximate the second attachment region and adjacent the base of the thumb portion on the back side of the glove such that the pad is configured to cushion a carpometacarpal joint adjacent the dorsal subluxation of the user of the brace from impact,
   wherein the pad further comprises a reinforcement member disposed on the palm side of the glove and wherein at least a portion of the first elastic strap is aligned with the reinforcement member.

2. The thumb brace of claim 1 wherein the pad is enclosed by a cover.

3. The thumb brace of claim 2 wherein the cover is attached to the back side of the glove.

4. The thumb brace of claim 3 wherein the first end of the first strap is attached to the cover, to the glove proximate the cover, or both.

5. The thumb brace of claim 4 wherein the first end of the first strap is attached to the cover via stitching, to the glove proximate the cover via stitching, or both.

6. The thumb brace of claim 1 wherein the reinforcement member is attached to at least a portion of the first strap.

7. The thumb brace of claim 6 wherein the reinforcement member is attached to at least a portion of the first strap via stitching.

8. The thumb brace of claim 4 wherein the reinforcement member is attached to at least a portion of the first strap.

9. The thumb brace of claim 8 wherein the reinforcement member is attached to at least a portion of the first elastic strap via stitching.

10. The thumb brace of claim 1 wherein the pad and the reinforcement member are an integral structure molded from silicon rubber.

11. The thumb brace of claim 9 wherein the pad and the reinforcement member are an integral structure molded from silicon rubber.

12. The thumb brace of claim 10 wherein the glove is a golf glove.

13. A thumb brace comprising:
    a glove comprising first, second, and third hook and loop fasteners, wherein the first hook and loop fastener provides an adjustable cuff opening for the glove;
    the second hook and loop fastener connects first, second, or both ends of a first elastic strap positioned on the glove and configured to extend a distal end of a gloved thumb metacarpal bone of a gloved hand of a user of the glove; and
    the third hook and loop fastener connects a second end of a second elastic strap positioned on the glove and configured to reduce a dorsal subluxation at a proximal end of the gloved thumb metacarpal bone of the gloved hand of the user of the glove; and
    a pad attached to the glove and positioned proximate a base of a thumb portion of the glove such that the pad is configured to cushion a carpometacarpal joint adjacent the dorsal subluxation of the user of the brace from impact,
    wherein the pad further comprises a reinforcement member disposed on a palm side of the glove and wherein at least a portion of the first elastic strap is aligned with the reinforcement member.

14. The thumb brace of claim 13 wherein the pad is enclosed by a cover.

15. The thumb brace of claim 14 wherein the reinforcement member is attached to at least a portion of the first strap.

16. The thumb brace of claim 15 wherein the reinforcement member is attached to at least a portion of the first strap via stitching.

17. The thumb brace of claim 16 wherein the pad and the reinforcement member are an integral structure molded from silicon rubber.

18. The thumb brace of claim 17 wherein the first end of first strap is attached to the cover, to the glove proximate the cover, or both.

19. The thumb brace of claim 18 wherein the glove is a golf glove.

20. A method of using a thumb brace comprising a glove, a pad, and a strap system, the method comprising:

placing the glove on a hand experiencing subluxation of the thumb metacarpal bone;

extending a distal end of the gloved thumb metacarpal bone of the gloved hand by releasably connecting a first elastic strap of the strapping system to a first attachment region on the glove;

reducing a dorsal subluxation at a proximal end of the gloved thumb metacarpal bone of the gloved hand by releasably connecting a second elastic strap to a second attachment region of the glove, and cushioning a carpometacarpal joint adjacent the dorsal subluxation of the user of the brace from impact via the pad, wherein the pad further comprises a reinforcement member disposed on a palm side of the glove and wherein at least a portion of the first elastic strap is aligned with the reinforcement member.

* * * * *